(12) United States Patent
Terakawa et al.

(10) Patent No.: US 6,451,537 B1
(45) Date of Patent: Sep. 17, 2002

(54) GENE OF RICE DIHYDRODIPICOLINATE SYNTHASE AND DNA RELATING TO THE SAME

(75) Inventors: Teruhiko Terakawa; Hisakazu Hasegawa, both of Atsugi; Masanori Yamaguchi, Zama, all of (JP)

(73) Assignee: Hokko Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/673,397

(22) PCT Filed: Apr. 17, 1998

(86) PCT No.: PCT/JP98/01784

§ 371 (c)(1),
(2), (4) Date: Nov. 30, 2000

(87) PCT Pub. No.: WO99/54483

PCT Pub. Date: Oct. 28, 1999

(51) Int. Cl.[7] .................................................. C12Q 1/68
(52) U.S. Cl. ..................... 435/6; 435/91.1; 435/91.2; 435/5; 530/350; 530/531
(58) Field of Search .............. 435/5, 6, 91.1, 435/91.2; 350/530, 531

(56) References Cited

PUBLICATIONS

Kaneko et al. Molecular Cloning of Wheat Dihydrodipicolinate Synthase. J. Biol. Chem. vol. 265, pp. 17451–174355. 1990.*

* cited by examiner

Primary Examiner—W. Gary Jones
Assistant Examiner—Janell E. Taylor
(74) Attorney, Agent, or Firm—Larson & Taylor PLC

(57) ABSTRACT

In accordance with this invention, there is provided a DNA sequence which can encode an enzyme protein functioning as the rice dihydrodipicolinate synthase (DHDPS). One example of the DNA sequence according to this invention is the DNA having the nucleotide sequence shown in SEQ ID No. 1 of Sequence Listing. Additionally, this invention provides the DNA having the nucleotide sequence of SEQ ID No. 5, as well as the DNA having the nucleotide sequence of SEQ ID No. 7 of Sequence Listing, as the DNA which is capable of encoding the protein having the DHDPS activity. When cultivation is made of the plant cells in which there has been introduced a recombinant vector having carried therein a DNA fragment containing the DNA of this invention as inserted at downstream of the promoter of said recombinant vector, it is feasible to regenerate from said plant cells a transgenic plant having a high lysine content.

3 Claims, 2 Drawing Sheets

SS: PHOSPHINOTHRICIN-RESISTANT GENE

US 6,451,537 B1

GENE OF RICE DIHYDRODIPICOLINATE SYNTHASE AND DNA RELATING TO THE SAME

FIELD OF THE INVENTION

The present invention relates to a gene capable of encoding the dihydrodipicolinate synthase of rice (*Oryza sativa*), and also to a DNA which relates to said gene. More specifically, this invention relates to novel DNAs for encoding such dihydrodipicolinate synthase of rice which participates in the lysine biosynthetic pathway in rice plant. Additionally, the invention relates to DNAs for encoding novel proteins having the activity of the dihydrodipicolinate synthase. Still additionally, the invention encompasses *Escherichia coli* as transformed by introduction of said novel DNA, as well as such transgenic plants as transformed by said novel DNA, and the seeds of such transgenic plants.

Still more additionally, this invention encompasses novel recombinant vectors in which said novel DNA has been inserted.

BACKGROUND ART

The grain seeds of cereal plants such as rice, corn and wheat are important nutritious sources for humans, cattle and others. However, these grain seeds are nutritionally of a more or less poor value, because of their low contents of lysine as one of the essential amino acids. It has been desired to create a new variety of plant which is capable of generating a cereal seed with a high lysine content and of a high nutritional value.

It has been known that, in a diaminopimelic acid-producing pathway of the lysine biosynthetic pathway in plants, a condensation binding takes place between aspartic acid-β-semialdehyde and pyruvic acid under the action of the dihydrodipicolinate synthase (sometimes abbreviated as "DHDPS" hereinafter) to produce 2,3-dihydropicolinic acid, from which diaminopimelic acid is then produced by enzymatic reactions through 5 steps, and that lysine is produced from the diaminopimelic acid as produced (Experimental Lecture Series of Biochemistry, Vol. 11, pp. 511–517, Tokyo Chemical Dojin). It is known that DHDPS is an enzyme protein having an activity to produce 2,3-dihydropicolinic acid by involving the condensation binding between aspartic acid-β-semialdehyde and pyruvic acid.

A report tells that the lysine content in the seed of a useful plant such as corn (*Zea mays*), tobacco (*Nicotiana tabacum*), rape seed (*Brassica campesteris*) and soybean (*Glycine max*) can be enhanced by introduction of the gene for encoding DHDPS, that is, the DHDPS gene, into the plant and then expressing the function of said gene in the transformed plant (PCT International Publication WO 95/15392, JP-W-7-504821, and "Biotechnology", Vol. 13, pp. 577–582, 1995).

The DHDPS genes have been isolated already from the plants of wheat, corn, soybean and tobacco. The nucleotide sequences of the DNA of these DHDPS genes have been elucidated. For example, the following techniques are reported in a number of literatures.

(1) The analysis of the amino acid sequence of wheat DHDPS, and the isolation of the DHDPS gene from wheat (JP-A-3-127984).

(2) The isolation of DHDPS gene from corn, and the nucleotide sequencing of the DNA of said gene (Molecular & General Genetics, Vol. 228, pp. 287–293, 1991).

(3) Transformation of corn by means of a DNA as obtained by a modification of the DNA of the DHDPS gene of corn, and the over-production of the lysine content in the corn seed (U.S. Pat. No. 5,545,545).

(4) A DNA as obtained by such a modification of the DNA of the tobacco DHDPS gene that a transgenic plant as transformed by the modified DNA is made free from the sensitivity of the DNA-encoded DHDPS to the feed-back inhibition by lysine, so that the lysine content in the transgenic plant can be over-produced (The Plant Journal, Vol. 8, No. 5, pp. 733–743, 1995).

(5) Soybean DHDPS gene (Plant Molecular Biology, Vol. 26, pp. 989–993, 1994).

(6) A method for over-producing the lysine content in a plant seed, which comprises transformation of the plant with using a DHDPS gene as derived from a bacterial species, for example, *Escherichia coli* (European Patent Application Publication No. 0 485 970 A2).

To the best of the knowledge of the present inventors, no literatures have been known, which report an analysis of the amino acid sequence of the rice DHDPS or which report a recovery of the gene of the rice DHDPS or the utilization of the rice DHDPS gene.

It is an object of this invention to provide the rice DHDPS gene which is produced from the rice plant. It is another object of this invention to provide several novel DNAs for encoding a protein having the rice DHDPS activity. It is still another object of this invention to transform useful plants such as corn, rice, soybean, wheat and barley by using said novel DNA for encoding a protein having the DHDPS activity, and to provide such a novel transgenic variety of a useful plant which has gained an ability to generate a seed of a high lysine content.

Any further objects of this invention will be apparent in the following descriptions.

DISCLOSURE OF THE INVENTION

In order to attain the above described various objects, the present inventors have now made a series of investigations. A first investigation has been carried out in order to produce the DHDPS gene from the rice plant. To obtain consequence of the investigations, the present inventors have conducted some experiments wherein the total RNA was extracted from a young rice plant, for example, disrupted green stem and leave, by a method known in the genetic engineering technology; and wherein from the so extracted total RNA was then isolated mRNA by a conventional method; and wherein from said mRNA were successfully produced cDNAs by a commercially available cDNA synthesis kit. It has now been found from the results of a great number of the inventor's empirical experiments that, when the resulting cDNAs mentioned above are conjugated to a such phage vector which had been prepared by treating the EcoRI cleavage end of a DNA fragment of a phage vector λgt11 (commercially available from STRATAGEN, LTD.) with a calf small intestine-derived alkaline phosphatase, there can be produced replicable recombinant λ phages.

It has now further been found that when *Escherichia coli* Y1088 strain is infected with said recombinant λ phages and then incubated, there can be produced a large number of recombinant λ phages in the forms of numerous plaques comprising the lysogenized bacteria cells; and that the numerous recombinant λ phages present in the resulting numerous plaques are composed of a wide variety of the phages containing therein the aforesaid rice-derived cDNAs and can thus be utilized as a cDNA library of rice.

With reference to the amino acid sequence of the wheat DHDPS protein as described in JP-A-3-127984 and also to one speculative nucleotide sequence of the wheat DHDPS gene, as well as to the nucleotide sequence of the corn DHDPS gene as described in the literature "Molecular & General Genetics", Vol. 228, pp. 287–293 (1991), the present inventors have now chemically synthesized a first oligonucleotide comprising 25 nucleotides, as well as a second oligonucleotide comprising 24 nucleotides, which are both believed to be appropriate to be used as primers for PCR method.

When a mixture of the aforesaid rice cDNA library (namely, the above-mentioned recombinant λ phages) with the first oligonucleotide and the second oligonucleotide as above has been used to conduct amplification of DNA by PCR method, it has now been found that the first and second oligo-nucleotides can serve as the primers (the complementary DNA) which to be required for the PCR method, and that the cDNAs present in the rice cDNA library can serve as the template, so that a part of the rice DHDPS gene-derived cDNA can be amplified. The present inventors can have then successfully produced an amplified product of said part of the rice DHDPS gene-derived cDNA, as a probe DNA, from the resulting PCR amplification mixture.

The present inventors have used the so produced probe DNA as a screening material to carry out the phage plaque hybridization method, and then there has been got a success fortunately to isolate such four plaques comprising the recombinant λ phages having integrated with the said rice DHDPS gene, from said previously produced rice cDNA library (composed of 300,000 plaques comprising said recombinant λ phages), as results of numerous empirical experimental procedures through try and error. The thus isolated four plaques comprising the recombinant λ phages have now been separately amplified, and the present inventors have isolated and produced the four types of the individual λ phage DNAs by a conventional method. The four types of the phage DNA thus produced have then been individually cleaved with a restriction endonuclease EcoRI to produce DNA fragments. When making comparison of the resulting DNA fragments with each other, it has been indicated that these DNA fragments have the same nucleotide sequence. From further comparison of said DNA fragments as produced with the known DNA sequences of the DNA segments of the wheat DHDPS gene and corn DHDPS gene, the present inventors can have concluded to approve that the said DNA fragments contain the DNA sequence which is corresponding to the rice DHDPS gene.

The said produced DNA fragments, which are now found to contain such DNA sequence that corresponds to the rice DHDPS gene, have been cleaved with a restriction endonuclease EcoRI. Then, the resultant DNA fragment produced by this cleavage has been inserted into and ligated to the EcoRI cleavage site of a commercially available, known plasmid vector pBluescript II SK(+), by using a DNA ligation kit. The recombinant plasmid vector so produced can be used to transform *Escherichia coli* XL1-Blue MRF' strain. The resulting *Escherichia coli* transformant cells can be incubated to produce a great number of copies of the bacterial cells. From these bacterial cells so copied is produced the plasmid. Then, a DNA fragment which contains the rice-derived DNA sequence therein is cleaved out of the DNA of the so produced plasmid, by using the restriction enzymes. The DNA fragment as obtained by this cleavage is then subjected to DNA sequencing, whereby it has been confirmed that the nucleotide sequence of the DNA sequence, which is inserted in the latter DNA fragment and which has been approved to correspond to the rice DHDPS gene, just exhibits a nucleotide sequence which is described in SEQ ID No. 1 of Sequence Listing given hereinafter.

To the best of the knowledge of the inventors, it has also been found that the DNA having the nucleotide sequence shown in SEQ ID No. 1 of Sequence Listing is a novel DNA which is never described in any literature.

It is considered that the protein as encoded by the DNA having the nucleotide sequence of SEQ ID No. 1 is a protein having the amino acid sequence shown in SEQ ID No. 2 of Sequence Listing, and that the said protein constitutes the rice DHDPS.

In a first aspect of the invention, therefore, there is provided a DNA for encoding the rice dihydrodipicolinate synthase which has the amino acid sequence shown in SEQ ID No. 2 of Sequence Listing hereinafter.

More specifically, the DNA according to the first aspect of the invention may be a DNA having the nucleotide sequence shown in SEQ ID No. 1 of Sequence Listing.

The DNA according to the first aspect of the invention is a DNA which encodes the protein of the rice DHDPS. As described above, the DNA of this invention is produced from the cDNA library of rice by the genetic engineering technique through the investigations of the inventors. Because the nucleotide sequence of the DNA of this invention once has been elucidated as above in accordance with the invention, said DNA can be produced also by chemical synthesis with reference to the nucleotide sequence of SEQ ID No. 1 of Sequence Listing. By polymerase chain reaction (abbreviated as PCR) or hybridization, it is also possible to produce the DNA of the first aspect of the invention from the DNA library of the rice chromosome in such a way that either a synthetic oligonucleotide as prepared with reference to the nucleotide sequence of SEQ ID No. 1 is used as a probe, or said synthetic oligonucleotide is used as a primer.

The method for producing the DNA of the first aspect of the invention from the stem and leave of rice by the genetic engineering technology is schematically described hereinbelow.

(1) Preparation of Rice mRNA and Construction of the cDNA Library of Rice

From various tissues of rice plant, for example, stem and leave, root and callus of *Oryza sativa* (rice), preferably green stem and leave thereof, there is extracted a total RNA in a conventional manner. From the so extracted total RNA are then removed contaminants such as protein. The resulting partially purified total RNA fraction is passed through a column of oligo dT cellulose to purify the poly(A)$^+$ RNA, so that the MRNA of rice can be obtained.

Subsequently, the rice cDNAs are synthetically prepared by using said mRNA of rice by means of a commercially available cDNA synthesis kit. The so synthesized cDNAs are inserted into a phage vector, for example, λgt11 vector or λZAPII vector, to produce a great number of the recombinant phages. With these recombinant phages are then infected the cells of *Escherichia coli* as host cell, followed by incubation, so that a great number of the recombinant phages is produced in the plaques of the lysogeized host cells. A series of these procedures can be practiced by using any commercially available cDNA cloning kit.

Such great number of the recombinant phages as obtained in the plaques of the lysogenized host cells of *Escherichia coli* are comprising a wide variety of the phages containing therein the cDNAs as derived from rice, and hence the said recombinant phages can be utilized as the cDNA library of rice.

(2) Construction of Primers for PCR Method

By comparing the known nucleotide sequence of the wheat DHDPS gene (for example, the DNA sequence as described in JP-A-3-127984) with the known nucleotide sequence of the corn DHDPS gene (for example, the DNA sequence as described in Molecular & General Genetics, Vol. 228, pp. 287–293), the present inventors have now detected that there exists a nucleotide sequence which is retained in common to the aforesaid known two nucleotide sequences. With reference to the common nucleotide sequence thus detected, the present inventors have chemically synthesized and constructed two types of oligonucleotides (namely, the oligonucleotides of SEQ ID Nos. 3 and 4 described in Sequence Listing hereinafter) to be used as the primers (the complementary DNA) for PCR method.

(3) Preparation of Probe DNA

For the end to selectively amplify the desired DNA of encoding the rice DHDPS present within the rice cDNA library which was produced as above in the form of the plaques containing a great number of the recombinant phages, amplification of the DNA of encoding a part of the rice DHDPS gene is done with utilizing the rice cDNA library as the template, according to the PCR method and with using the said two synthetic oligonucleotide as the primer.

After the PCR amplification is done in repetition, the amplified product of such a DNA fragment, which is the part of the DNA sequence corresponding to the rice DHDPS gene, is recovered and collected as the probe DNA from the resultant amplification mixture.

(4) Selection of DNA of the Rice DHDPS Gene from the Rice cDNA Library

Then, several numbers of plaques made of the recombinant phages having the inserted DNA sequence, which is wholly corresponding to the target DHDPS gene of rice, are selected and separated from the great number of said plaques made of the recombinant phages which were previously produced as the rice cDNA library. This selection and separation may be done according to a phage plaque hybridization method with using the said probe DNA as the screening material.

Thereby, a DNA fragment carrying therein the target DNA sequence, which is corresponding to the DNA of the rice DHDPS gene, can be harvested in the form of the recombinant phage having the said DNA fragment inserted therein.

Thus, the recombinant phages provided in the form of the plaques as selected by the aforesaid plaque hybridization method are separated and collected. Then, the phage DNA is harvested from the so collected recombinant phages. By treating the so harvested phage DNA by the dideoxy method and the like, it is feasible to decide the nucleotide sequence of the inserted DNA fragment which has been derived from rice. When the amino acid sequence, which shall be defined by the protein-encoding region (the open reading frame) of the nucleotide sequence of the said inserted DNA fragment as just derived from rice, is compared with the known amino acid sequence of the corn DHDPS protein or of the wheat DHDPS protein, followed by determining the presence or absence of the homology between them, it can be identified whether or not the said inserted DNA fragment contains the DNA sequence which is just corresponding to the rice DHDPS gene.

Thus, the above-mentioned, inserted DNA fragment, which has been identified to contain therein the DNA sequence just corresponding to the rice DHDPS gene, can then be cleaved out and recovered from the phage DNA of the aforesaid recombinant phages which was selected and collected in the aforementioned method.

(5) Cloning of the cDNA Corresponding to the Rice DHDPS Gene

The DNA, which was produced by cleaving the recombinant phages and was obtained as the DNA fragment containing therein the DNA sequence of the rice DHDPS gene as described above, is then used to construct a recombinant plasmid vector, by inserting and ligating the said DNA as produced just from the recombinant phages, into the EcoRI cleavage site of a plasmid vector pBluescript II SK(+). The thus constructed recombinant plasmid vector is then used to transform *Escherichia coli* XL1-Blue MRF'. By culturing and proliferating the *Escherichia coli* transformant cells thus produced, there can be cloned the said recombinant plasmid which carries the DNA fragment containing therein the inserted DNA sequence of the rice DHDPS gene. In this way, the DNA fragment which contains therein the DNA sequence of the rice DHDPS gene can be cloned.

(6) Sequencing of the Cloned DNA

The so cloned recombinant plasmid is then separated and cut with appropriate restriction enzymes to produce such a DNA fragment which contained therein the DNA sequence of the DHDPS gene of rice. By treating the so produced DNA fragment with a commercially available nucleotide sequencing kit, it is possible to determine the nucleotide sequence of the DNA which comprises the DNA sequence just corresponding to the rice DHDPS gene. The thus determined nucleotide sequence of the DNA which encodes the rice DHDPS gene is just as described in SEQ ID No. 1 of Sequence Listing.

When the DNA sequence obtained as above by the first aspect of the invention or a DNA fragment comprising said DNA sequence is used as a probe, the DNA of the DHDPS gene can be obtained also from the chromosome of rice itself in a conventional manner. The DNA of the DHDPS gene which is so obtained from the rice chromosome itself may possibly contain an intron. Such DNA having the intron intervened therein is also encompassed within the scope of the DNA of the first aspect of the invention, so far as it is the DNA for encoding the rice DHDPS.

The DNA fragment of the nucleotide sequence, which is described in SEQ ID No. 1 of Sequence Listing and was prepared in the following Example 1, and which contains therein the DNA sequence corresponding to the rice DHDPS gene, is inserted and ligated into a pBluescript II SK(+) plasmid vector to prepare a recombinant plasmid vector. *Escherichia coli* XL1-Blue MRF' which has been transformed by introduction of the above prepared recombinant plasmid vector, is designated as *Escherichia coli* DAP8-1 strain and was deposited under Accession No. of FERM P-15906 on Oct. 14, 1996 at the National Institute of Bioscience and Human-Technology, the Agency of Industrial Science and Technology, at Tsukuba-City, Ibarak-ken, Japan. Further, the *Escherichia coli* DAP8-1 strain has been deposited at the same institute, under Accession No. of FERM BP-6310, since Mar. 26, 1998, under the provisions of the Budapest Treaty.

The DNA according to the first aspect of the invention is useful in that said DNA enables a great quantity of the rice DHDPS protein to be produced by chemical synthesis, when the nucleotide sequence of the DNA as elucidated in accordance with the invention is employed as a guideline. Further, the DNA of this invention can contribute a lot to a progress of the enzymological investigative works of the rice DHDPS protein.

Furthermore, a recombinant vector may be constructed when the terminus of either the DNA sequence as provided by the first aspect of the invention or of an appropriate DNA fragment containing therein said DNA sequence are linked to EcoRI linkers, followed by inserting the resulting linked DNA sequence or DNA fragment into such EcoRI cleavage site of a commercially available plasmid vector pTV118N (manufactured by TAKARA Shuzo Co., Ltd., Japan), which is present at downstream of the Eac promoter of the vector. It is expected that, when *Escherichia coli* which has been transformed with the resulting recombinant vector so constructed as above is cultured, the transformed cells of *Escherichia coli* can intracellularly generate such a protein which has the DHDPS activity. Thus, a protein having the rice DHDPS activity can be expectedly produced in a culture of the *Escherichia coli* cell which has been transformed by insertion of the above recombinant vector such that the so transformed *Escherichia coli* cell can express the DNA of the first aspect of the invention.

Meanwhile, it has generally been known widely by a person of an ordinary skill in the art, that even such an amino acid sequence, which is produced by a modification of an intact amino acid sequence of a protein having a physiological activity, through a deletion of one or plural amino acids, and/or through replacement thereof by other amino acids, and/or through addition of one or plural amino acids to the intact amino acid sequence, is possible to retain the physiological activity of the parent protein having said intact amino acid sequence. The DNA according to the first aspect of the invention is able to encode the protein having the DHDPS activity, even when a part or plural parts of the nucleotide sequence of the DNA of the first aspect of this invention has or have been modified.

In other words, the novel DNA according to the first aspect of the invention can retain the ability to encode the protein having the DHDPS activity, even after one or plural nucleotides, for example, 1, 2 or 3 to 10 nucleotides present in the nucleotide sequence of the DNA of the first aspect of this invention has or have been modified with other nucleotides.

In a second aspect of the invention, therefore, there is provided a DNA for encoding such a protein which has the dihydrodipicolinate synthase activity, and which protein has such an amino acid sequence that is formed by modification of the amino acid sequence shown in SEQ ID No. 2 of Sequence Listing, with said modification being made by deletion of one or plural amino acids from said amino acid sequence of SEQ ID No. 2, and/or by replacement of one or plural amino acid present in said amino acid sequence by other amino acids, and/or by insertion or addition of other amino acids to said amino acid sequence.

The DNA of the second aspect of the invention is thus such a DNA which has been modified from the DNA of the first aspect of the invention. Thus, the DNA of the second aspect of the invention can be produced by modifying the nucleotide sequence of the DNA of the first aspect of the invention, for example, by making a site-directed mutagenesis, in such a way that the resulting nucleotide sequence as modified can encode a protein having such an amino acid sequence which is modified by deletion, replacement or addition of an amino acid (or amino acids) at specific site(s) of the protein that is encoded by the DNA of the first aspect of the invention.

The modified DNA of the second aspect of the invention can be produced also by subjecting the bacterial cells having a DNA fragment containing therein the DNA of the first aspect of the invention to a mutation process, and subsequently selectively recovering from the resulting mutated cells, for example, a DNA having such a nucleotide sequence which is hybridizable with the DNA of the nucleotide sequence of SEQ ID No. 1 of Sequence Listing under stringent conditions, but which is partially different from the nucleotide sequence of SEQ ID No. 1. The term "stringent conditions" herein referred to does mean such conditions under which any hybrid which is specific to the DNA of the first aspect of the invention is formed, while a hybrid which is non-specific to said DNA is not formed. The stringent conditions can hardly be defined or specified numerically. However, one typical example of the stringent conditions is such one which can permit the hybridization of two nucleic acids or DNAs to take place at a high homology, for example, at a 98% or higher homology, but can inhibit the hybridization of two nucleic acids from occurring at a homology of lower than the 98% value.

Thus, the DNA of the second aspect of the invention may be, for example, a DNA which is such a DNA having a nucleotide sequence partially different from the nucleotide sequence shown in SEQ ID No. 1 of Sequence Listing but having a high homology to said nucleotide sequence of SEQ ID No. 1, and which DNA can hybridize with the DNA having said nucleotide sequence shown in SEQ ID No. 1 of Sequence Listing under stringent conditions, and which DNA encodes the protein having the dihydrodipicolinate synthase activity.

Specifically, the DNA of the second aspect of the invention may be, for example, the DNA sequence which is designated as a modified DNA-158N sequence in Example 2 hereinafter and which is prepared according to the method described in Example 2, as well as the DNA sequence which is designated as a modified DNA-166A sequence in Example 3 hereinafter and which is prepared according to the method described in Example 3.

The DNA sequence, which is designated as the modified DNA-158N sequence, has the nucleotide sequence of SEQ ID No. 5 of Sequence Listing. The modified DNA-158N sequence corresponds to such a DNA which is formed by a modifying of the DNA of the nucleotide sequence of SEQ ID No. 1 of Sequence Listing, in such a way that the sequence AAC (a codon for encoding asparagine) present at the positions 472, 473 and 474 of the nucleotide sequence of the DNA of the first aspect of the invention is replaced by a sequence ATC (a codon for encoding isoleucine) with replacing the base A (adenine) at the position 473 by a base T (thymine). The modified DNA-158N sequence as above can hybridize with the DNA of the first aspect of the invention under the stringent conditions.

The protein, which is encoded by the modified DNA-158N sequence, has an amino acid sequence of SEQ ID No. 6 of Sequence Listing and has the DHDPS activity.

The modified DNA-166A sequence mentioned above has the nucleotide sequence of SEQ ID No. 7 of Sequence Listing. The modified DNA-166A sequence corresponds to such a DNA which is formed by modifying of the DNA of the nucleotide sequence of SEQ ID No. 1 of Sequence Listing, in such a way that the sequence GCA (a codon for encoding alanine) at the positions 496, 497 and 498 of the nucleotide sequence of the DNA of the first aspect of the invention is replaced by a sequence GTA (a codon for encoding valine) with replacing the base C (cytosine) at the position 497 by a base T (thymine). The modified DNA-166A sequence as above can hybridize with the DNA of the first aspect of the invention under the stringent conditions.

The protein, which is encoded by the modified DNA-166A sequence, has an amino acid sequence of SEQ ID No. 8 of Sequence Listing and has the DHDPS activity.

Additionally, a further example of the DNA of the second aspect of the invention may be specifically a DNA sequence having such a nucleotide sequence which is prepared by replacing the adenine at the position 473 of by the nucleotide sequence of SEQ ID No. 1 of Sequence Listing by thymine, and also by replacing the cytosine at the position 497 by thymine. This DNA sequence so modified may encode a protein having the dihydrodipicolinate synthase activity, and having such an amino acid sequence which is prepared by replacing the asparagine at the position 158 of the amino acid sequence of SEQ ID No. 2 of Sequence Listing by isoleucine and also by replacing the alanine at the position 166 by valine.

Generally, as the methods for modifying a nucleotide sequence present in a part of a DNA sequence, there are known several methods, including the Kunkel method (Methods in Enzymology, Vol. 154, No. 367), and the oligonucleotide-direct dual amber method and other methods.

The essential object of this invention is to create a novel transgenic plant species which is so transformed to generate a seed of a high lysine content. Hence, this invention requires such a modified DHDPS which can exhibit an enzyme activity so modified that the resulting enzyme activity of the modified DHDPS is made insensitive to that the DHDPS participating in the lysine bio-synthetic pathway can involve the feed-back inhibition owing to the bio-product, lysine. As well, this invention requires such a DNA which can encode said modified DHDPS. For the purpose of preparing from the DNA of the first aspect of the invention, a novel modified DNA capable of encoding such a novel DHDPS which has been so modified that the resultant modified novel DHDPS enzyme is freed from the sensitivity to the feed-back inhibition by lysine, the inventors have now made some investigations at first. Consequently, the inventors have now found that one or two or more bases, which is or are present in partial regions of the nucleotide sequence of encoding the rice DHDPS according to the first aspect of the invention, can be replaced by other bases by means of a combination of a modified method of the known Kunkel method with a modified oligonucleotide-direct dual amber method.

With making reference to the prior art for the modification of the corn DHDPS gene as described in the U.S. Pat. No. 5,545,545, the prior art for the modification of the tobacco DHDPS gene as described in The Plant Journal, Vol. 8, No. 5, pp. 733–743, and the prior art for the plant transformation with using the bacterial DHDPS gene as described in the European Patent Application 0 485 970 A2, furthermore, the inventors have now studied and got a speculation that such a modified DNA, which is prepared either by replacing the base adenine (A) at the position 473 by thymine (T) or replacing the cytosine (C) by thymine (T) at the position 497 of the nucleotide sequence of the DNA of the first aspect of the invention as shown in as SEQ ID No. 1 of Sequence Listing, would be able to encode a novel modified enzyme protein which retains the DHDPS activity, and of which enzyme activity is made insensitive to the feed-back inhibition by lysine.

Based on the above speculation, the inventors have now made various investigations and empirical experiments at a great number of times. Consequently, the inventors have now found that the undermentioned recombinant plasmid vector (referred to as "pDAP8-1" hereinafter) is suitable as a starting material for the preparation of the novel modified DNA as desired above. Said plasmid vector pDAP8-1 has been prepared by inserting and integrating the aforesaid DNA fragment containing therein the DNA sequence of the rice DHDPS gene as prepared upon the production of the novel DNA of the first aspect of this invention [(namely, the DNA fragment of the recombinant λ phage, i.e. the DNA fragment containing the DNA sequence of SEQ ID No. 1 (referred to as DHDPS-DNA-1143 sequence hereinafter)] into the position between the EcoRI cleavage site and the SacI cleavage site of the plasmid vector pbluescript II SK (+) by using a DNA ligation kit.

Additionally, the inventors have now chemically synthesized five types of primers suitable for preparing the above-mentioned target novel modified DNA from the starting recombinant plasmid vector pDAP8-1 according to the PCR methods. Thus, the inventors have prepared a primer No. 3 comprising an oligonucleotide of the nucleotide sequence of SEQ ID No. 9 of Sequence Listing; a primer No. 4 comprising an oligonucleotide of the nucleotide sequence of SEQ ID No. 10 of Sequence Listing; a primer FW-1 comprising an oligonucleotide of the nucleotide sequence of SEQ ID No. 11 of Sequence Listing; a primer RV-1 comprising an oligonucleotide of the nucleotide sequence of SEQ ID No. 12 of Sequence Listing; and a primer BS KPN-1 comprising an oligonucleotide of the nucleotide sequence of SEQ ID No. 13 of Sequence Listing.

When the method described below in detail has been done with using the plasmid vector pDAP8-1 and the above-mentioned five types of the primers comprising the synthetic oligonucleotides, the inventors now can have successfully produced some specific examples of the modified DNA of the second aspect of the invention. These specific examples are a DNA fragment containing the DNA of SEQ ID No. 5 of Sequence Listing, namely a DNA fragment containing the modified DNA-158N sequence, as well as a DNA fragment containing the DNA of SEQ ID No. 7 of Sequence Listing, namely a DNA fragment containing the modified DNA-166A sequence.

Not only the DNA of the first aspect of the invention, but also the modified DNA-158N sequence and the modified DNA-166A sequence may be inserted in the recombinant vector and then may be introduced in the rice plant according to the known method for integrating an exogenous gene into plants as described hereinafter in Example 4 or 5, so that the introduced DNA can express in the resulting transgenic plant as transformed.

It is verified that the transgenic plant of rice as transformed by the DNA of the first aspect of the invention or by the modified DNA-158N sequence or the modified DNA-166A sequence of the second aspect of this invention, can generate a rice plant cell or a rice seed having an enhanced lysine content.

Next, a brief description is given of the method for modifying DNA which comprises procedures typically illustrated below in Example 2, and which can suitably be used for preparing the DNA fragment containing the modified DNA-158N sequence of the second aspect of the invention.

(1) Cloning of the DNA of the First Aspect of the Invention

By inserting and conjugating the DNA fragment containing the DNA having the 1143 nucleotides of SEQ ID No. 1 of Sequence Listing of the first aspect of the invention, (namely the DNA fragment containing the aforesaid DHDPS-DNA-1143 sequence) into the EcoRI cleavage site of the vector pBluescript II SK(+) by means of a DNA ligation kit, there can be produced the recombinant plasmid vector pDAP8-1. After introduction of this plasmid vector pDAP8-1 in the *Escherichia coli* XL1-Blue MRF' strain, the resulting transformed cells of *Escherichia coli* are proliferated. From the resulting copies of the transformed *Escherichia coli* cells, there can be extracted a great quantity of the recombinant plasmid vector pDAP8-1, according to a conventional method. The plasmid vectors so obtained contain a great number of the copies of the DNA fragment containing the DHDPS-DNA-1143 sequence. Thus, it is confirmed that the DNA of the first aspect of the invention is cloned as above.

(2) Construction of Primers for PCR Method

Using a DNA synthesizer (Model-391; manufactured by Applied Biosystems, Co.), five types of the oligonucleotides having the following nucleotide sequences are synthetically prepared as the primers.

(a) Primer No. 3 (primer having the following nucleotide sequence as shown in SEQ ID No. 9 of Sequence Listing)
5'-GCCTCTCTTGTTGAGATACTACCTGTGTTGCC-3'

(b) Primer No. 4 (primer having the following nucleotide sequence as shown in SEQ ID No. 10 of Sequence Listing)
5'-GCAAATCCCTGCTCTGTTACATGAATAGCC-3'

(c) Primer No. FW-1 (primer having the following nucleotide sequence as shown in SEQ ID No. 11 of Sequence Listing)
5'-GTAAAACGACGGCCAGTGAG-3'

(d) Primer No. RV-1 (primer having the following nucleotide sequence as shown in SEQ ID No. 12 of Sequence Listing)
5'-GGAAACAGCTATGACCATG-3'

(e) Primer No. BS KPN-1 (primer having the following nucleotide sequence as shown in SEQ ID No. 13 of Sequence Listing)
5'-TAGGGCGAATTGTGTGTACCG-3'

(3) Amplification and Recovery of the Required DNA Fragment According to PCR Method For making the amplification of the required DNA fragment, there are conducted two reactions which are included by the first step of PCR method and which are namely the following reactions (A) and (B).

The reaction (A) comprises adding the recombinant plasmid vector pDAP8-1 for use as the template, as well as the primers FW-1 (the synthetic oligonucleotide of SEQ ID No. 11) and primer No. 3 (the synthetic oligonucleotide of SEQ ID No. 9, of which the GAT at the positions 15 to 17 from the 5' terminus can induce the ATC at the modified part of the DNA-158N sequence) to a conventional PCR reaction mixtutre [containing Tris-HCl, MgCl$_2$, KCl and 4 types of deoxynucleotide phosphates (dNTP) and La Taq DNA polymerase], and then progressing the amplification reactions therein. By the reaction (A), there can be produced a DNA fragment (referred to as DNA fragment-A) which has a nucleotide sequence corresponding to a part of the DHDPS-DNA-1143 sequence, through the amplification reactions.

The reaction (B) comprises adding the primer RV-1 (the synthetic oligonucleotide of SEQ ID No. 12) and primer BS KPN-1 (the synthetic oligonucleotide of SEQ ID No. 13), as well as the vector pDAP8-1 as the template to the conventional PCR reaction mixture of the same composition as that used in the reaction (A), and subsequently progressing the amplification reactions therein. By the reaction (B), there can be produced a DNA fragment (referred to as DNA-fragment B) which contains a nucleotide sequence corresponding to a part of the DHDPS-DNA-1143 sequence and which further contains an extension part having a SacI cleavage site at the 3' terminus thereof, through the amplification reactions.

The aforementioned amplification reactions by the PCR method can be practiced by using a commercially available PCR reactor.

After the completion of these amplification reactions, the amplification reaction solution coming from the reaction (A) is fractionated by a low-melting agarose electrophoresis, followed by cutting a gel band containing the DNA fragment-A of 480 bp (base pair) obtained as an amplified product, from the agarose gel. Additionally, the amplification reaction solution coming from the reaction (B) is similarly fractionated by a low-melting agarose electrophoresis, followed by cutting a gel band containing a DNA fragment-B of 1200 bp (base pair) obtained as an amplified product, from the agarose gel.

By purifying these two cut pieces of the gel bands with a DNA purification kit, for example, Geneclean II kit (manufactured by Funakoshi, Co., Ltd.), a purified product of the said DNA fragment-A and a purified product of the said DNA fragment-B are individually produced.

As the second step of the PCR method, there is conducted a process of preparing a DNA fragment of 1200 bp which contains therein a DNA sequence of such a nucleotide sequence as formed by replacing the adenine at the position 473 of the nucleotide sequence of SEQ ID No. 1 of sequence Listing by thymine (that is, the DNA sequence corresponding to the DNA-158N sequence of the nucleotide sequence of SEQ ID No. 3 as provided according to the second aspect of the invention), and which DNA fragment of 1200 bp contains an extension part having a KpnI cleavage site at the 5' terminus of said DNA sequence and having a SacI cleavage site at the 3' terminus thereof. To this end, the purified product of the DNA fragment-A (the sequence of 480-bp length) obtained as the amplify-cation product of the reaction (A) and the purified product of the DNA fragment-B (the sequence of 1200-bp length) obtained as the amplification product of the reaction (B)(both for use as the templates), as well as the primer RV-1 (the synthetic oligonucleotide of SEQ ID No. 12), and the primer FW-1 (the synthetic oligonucleotide of SEQ ID No. 11) are added to a conventional PCR reaction mixture [containing Tris-HCl, MgCl$_2$, KCl and 4 types of deoxynucleotide phosphates (dNTPs) and La Taq DNA polymerase], followed by progressing the amplification reactions therein. After the completion of the reactions, the resulting reaction solution is fractionated by a low-melting agarose electrophoresis, followed by cutting a gel band containing the objective DNA fragment of 1200 bp (referred to as DNA fragment-C), from the agarose gel.

By purifying the resultant cut gel band with a DNA purification kit, for example, Geneclean II kit (manufactured by Funakoshi, Co., Ltd.), a purified product of the DNA fragment-C is produced. This DNA fragment-C has such structure that this fragment carries therein the nucleotide sequence corresponding to the modified DNA-158N sequence of the second aspect of the invention and also contains an extension part having a KpnI cleavage site at the 5' terminus of the DNA fragment and an extension part having a SacI cleavage site at the 3' terminus thereof.

(4) Cloning of the DNA Fragment Containing the Modified DNA-158N Sequence

Next, the DNA fragment-C as produced in the above (3) is used to produce a DNA fragment which contains the target modified DNA-158A sequence (a first example of the modified DNA of the second aspect of the invention).

To this end, first, the extension parts present at the 5' and 3' termini of the above DNA fragment-C are treated with the restriction endonucleases KpnI and SacI.

Thereby, the DNA fragment-C is cut and divided to produce such a DNA fragment which carries therein the modified DNA-158A sequence, which contains the extension part having the SacI cleavage site at the 3' terminus and in which the 5' terminus starts at ATG.

In this way, a sample of the DNA fragment containing therein the DNA sequence corresponding to the target modified DNA-158A is obtained. Subsequently, the plasmid vector pBluescript II SK(+) is treated with restriction endonucleases KpnI and SacI, to produce a truncated plasmid which has the KpnI cleavage site at the 5' terminus and has the SacI cleavage site at the 3' terminus (and which is referred to as pBluescript II SK(+)-KpnI-SacI-truncated plasmid hereinbelow).

This KpnI-SacI-truncated plasmid is then mixed with said sample of the DNA fragment carrying therein the DNA-158N sequence, followed by subjecting the resultant mixture to a ligation reaction with using a DNA ligation kit, whereby there can be produced a recombinant plasmid containing the modified DNA-158N sequence (hereinafter referred to as pBluescript-DNA-158N plasmid).

After introducing the so produced recombinant plasmid in *Escherichia coli* XL1-Blue MRF' to effect the transformation thereof, the resulting transformed cells of *Escherichia coli* are cultured and proliferated in a liquid culture medium. A vast quantity of the proliferated bacteria cells of the transformed *Escherichia coli* is obtained, which contains copies of the recombinant plasmid, namely copies of the pBluescript-DNA-158N plasmid. In this way, the modified DNA-158N sequence can be cloned. From the cultured cells of the transformed *Escherichia coli* is extracted and harvested the desired plasmid containing the modified DNA-158N sequence, according to a routine method.

(5) Recovery of the Modified DNA-158N Sequence

The plasmid carrying therein the modified DNA-158N sequence which was recovered in the item (4), is treated and digested with restriction endonucleases XbaI and SacI.

Thus, a digestion solution can be prepared, which contains the DNA fragment carrying therein the modified DNA-158N sequence and further having the extension parts wherein the nucleotide sequence ATG is provided at the 5' terminus adjacent to the XbaI cleavage site, and wherein the SacI cleavage site is provided at the 3' terminus.

After the fractionation of the digestion solution is made by low-melting agarose electrophoresis, a gel band containing the said DNA fragment is cut from the agarose gel. The resulting cut piece of the agarose gel band is dissolved in a TE buffer, and the resulting solution is subjected to extraction with phenol. Thus, the said DNA fragment is recovered into the phenol extract solution. The phenol extract solution containing the said DNA fragment is mixed with an aqueous 3M sodium acetate solution and ethanol; and the resultant mixture is left to stand at 20° C. for about 6 hours, followed by centrifugation at a low temperature, to precipitate the DNA fragment. The precipitated DNA fragment is dried under reduced pressure, to afford the DNA fragment in the form of a powder, which is the fragment containing the target modified DNA-158N sequence. This powder of the DNA fragment carrying therein the modified DNA-158N sequence is soluble in water.

Furthermore, a DNA-modifying method which is preferably applicable to the preparation of a DNA fragment carrying therein the modified DNA-166A sequence according to the second aspect of the invention and which is illustrated in Example 3 hereinafter, may be practiced in the same way and by the same procedures as those for the above-mentioned method for preparing the DNA fragment carrying therein the modified DNA-158N sequence.

More specifically, the above-mentioned preferable method for preparing the DNA fragment carrying the modified DNA-166A sequence may comprise a first step of cloning the DNA sequence, wherein the recombinant vector pDAP8-1 containing the DNA of the first aspect of the invention (namely, DHDPS-DNA-1143) is introduced into *Escherichia coli* XL1-Blue MRF' and the transformed *Escherichia coli* cell is proliferated with following the same procedures as described in the item (1) of the foregoing Section of explaining the "Method for preparing the DNA fragment containing the modified DNA-158N sequence".

A subsequent step of the said preferable method comprises adding the vector pDAP8-1 for use as the template, as well as the primer FW-1 prepared as a synthetic oligonucleotide, and the primer No. 4 (the synthetic oligonucleotide of SEQ ID No. 10, which is capable of inducing the modified part "GTA" of the modified DNA-166A sequence due to the TAC located at the positions 18–20 from the 5' terminus of said oligonucleotide) to the conventional PCR reaction mixture of the same composition as that used in the reaction (A) described in the item (3) of the foregoing Section of explaining "Method for preparing a DNA fragment containing the modified DNA-158N sequence", and then effecting the amplification reactions therein. By the amplification reactions, there can be produced such a DNA fragment (referred to as DNA fragment-D) which carries therein a nucleotide sequence present in a certain region of the aforesaid DHDPS-DNA-1143 sequence.

In the very same manner as for the reaction (B) which is effected by the procedures described in the item (3) of the Section of explaining "Method for preparing a DNA fragment containing the modified DNA-158N sequence", there is subsequently conducted a reaction (B) step for PCR method. Thereby, the aforesaid DNA fragment-B is produced as amplification product from the reaction (B).

The above amplification solution which contains the DNA fragment-D as produced by the reaction (A) with using the primers FW-1 and No. 4, is then fractionated by low-melting agarose electrophoresis. Then, a gel band containing the DNA fragment-D of 480 bp as the amplification product is cut and separated out from the agarose gel. The amplification solution containing the DNA fragment-B as produced by the reaction (B) is similarly fractionated by low-melting agarose electrophoresis, and a gel band containing the DNA fragment-B of 1200 bp as the amplification product is cut and separated out of the agarose gel. Furthermore, these two cut pieces of gel bands are purified separately by using a DNA purification kit, and thereby individually a purified product of the DNA fragment-D and a purified product of the DNA fragment-B are prepared.

Additionally, there is conducted a second step of PCR method for preparing a 1200-bp DNA fragment which carries therein a DNA sequence as formed by a modification of the nucleotide sequence of SEQ ID No. 1 of Sequence Listing, with the base cytosine at the position 497 being replaced by thymine (namely, said DNA sequence is corresponding to the modified DNA-166A of the nucleotide sequence of SEQ ID No. 7), and which 1200-bp DNA fragment further contains an extension part having a KpnI cleavage site at the 5' terminus of the DNA fragment and also an extension part having a SacI cleavage site at the 3' terminus thereof. To this end, the purified product of the DNA fragment-D (said sequence of 480 bp) to be used as the template, and the purified product of the DNA fragment-B (said sequence of 1200 bp), as well as the primer RV-1 and the primer FW-1 are added to an amplification mixture for PCR method, followed by making subsequent amplification reactions therein. After the termination of the reactions, the amplification reaction solution obtained is fractionated by low-melting agarose electrophoresis. A gel band containing the desired DNA fragment of 1200-bp length (referred to as DNA fragment-E) is cut and separated out of the agarose gel.

The gel band so cut out is purified with a DNA purification kit, to produce a purified product of the DNA fragment-E. This DNA fragment-E has a structure such that this DNA fragment carries therein the nucleotide sequence corresponding to the modified DNA-166A sequence of the second aspect of the invention and also has an extension part having a KpnI cleavage site at the 5' terminus of the DNA fragment and has an extension part having a SacI cleavage site at the 3' terminus thereof.

The DNA fragment-E is used to produce a DNA fragment carrying therein the objective modified DNA-166A sequence (a second example of the modified DNA of the second aspect of the invention). For this purpose, the DNA fragment-E is treated with restriction endonucleases KpnI and SacI. Thereby, from the DNA fragment-E is cut out and separated a DNA fragment which carries therein the modified DNA-166A sequence, which contains an extension part having a SacI cleavage site at the 3' terminus of the DNA fragment, and of which the 5' terminus starts at ATG.

In such manner, a sample of the DNA fragment containing the DNA sequence corresponding to the modified DNA-166A sequence can be prepared. By subsequently ligating this DNA sample to the plasmid vector pBluescript II SK (+) with using a DNA ligation kit in the same way as described in the item (4) of the Section of explaining "Method for preparing the DNA fragment containing the modified DNA-158N sequence", there is produced a recombinant vector. Then, *Escherichia coli* XL1-Blue MRF' is transformed with the resulting recombinant vector, followed by progressing the proliferation of the resulting transformed *Escherichia coli* cell, and thus there can be cloned the plasmid containing the modified DNA-166A sequence.

Then, the thus cloned plasmid containing therein the modified DNA-166A sequence is recovered from the cultured cells of *Escherichia coli*. Then, the plasmid as recovered is treated in the same way as described in the item (5) of the Section of explaining "Method for preparing a DNA fragment containing the modified DNA-158N sequence". Thereby, a DNA fragment of 1143 bp can be prepared in the form of a water-soluble powder and this DNA fragment is a DNA fragment which carries therein the objective modified DNA-166A sequence.

In the above descriptions, the DNA fragment containing therein the modified DNA-158N sequence as well as the DNA fragment containing therein the modified DNA-166A sequence according to the second aspect of the invention have been prepared by a method of genetic engineering technology. With making reference to the nucleotide sequences described in SEQ ID No. 5 and No. 7, these two DNA fragments may be prepared also by conventionally known chemical synthesis of polynucleotides.

Specific embodiments of the second aspect of the invention are described in the above for such case where thymine replaces the adenine at position 473 or cytosine at position 497 of the nucleotide sequence of the DNA according to the first aspect of the invention. While, when the DNA of the first aspect of the invention is used as template and when a combination of synthetic oligonucleotides having appropriately prepared nucleotide sequences is used as primers, it is possible to prepare another modified DNA which has such a nucleotide sequence where a base present at a position away from the position 473 or 497 of the DNA of the first aspect of the invention has been replaced by another base.

Still further, the inventors have now further promoted additional investigations. Consequently, the inventors have now found that the novel DNA for encoding DHDPS according to the first aspect of the invention, as well as the novel modified DNA for encoding DHDPS according to the second aspect of the invention can be integrated into a recombinant vector and can then be introduced in a plant, so as to permit these DNAs to be expressed in the plant, when use is made of the conventionally known biotechnology manipulation procedures which comprise integrating an exogenous gene into a plant to transform the plant, and thereafter allowing the exogenous gene to express in the resulting transgenic plant.

In accordance with a third aspect of the invention, therefore, there is provided a transgenic plant characterized in that the plant comprises such plant cells that have been transformed by the integration of the plant cells with a recombinant vector which carries therein either the DNA for encoding the rice dihydrodipicolinate synthase according to the first aspect of the invention, or the DNA for encoding a protein having the dihydrodipicolinate synthase activity according to the second aspect of the invention, and wherein the inserted DNA is such one which can be expressed in the host cells.

The inventors now have additionally found that, when the transgenic plant as transformed by the integration of the DNA of the first or second aspect of the invention is such plant which can fructify a seed by cultivation of the plant, the seeds of the plant can be harvested by cultivating the transgenic plant under normal conditions.

In a fourth aspect of the invention, therefore, there is provided the seed of a transgenic plant, characterized in that said seed is recovered by cultivating the transgenic plant comprising such plant cells which have been transformed by the integration of the plant cells with a recombinant vector having carried therein the DNA for encoding the rice dihydrodipicolinate synthase according to the first aspect of the invention, wherein the inserted DNA can be expressed in the host cells, and then collecting the seed from the plant having fructified during cultivation of the plant.

In a fifth aspect of the invention, furthermore, there is provided the seed of a transgenic plant, characterized in that said seed is recovered by cultivating a transgenic plant comprising such plant cells which have been transformed by the integration of the plant cells with a recombinant vector having carried therein the DNA of the second aspect invention for encoding a protein having the dihydrodipicolinate synthase activity, wherein the inserted DNA can be expressed in the host cells, and then collecting the seed from the plant having fructified during the plant cultivation of the plant.

In a sixth aspect of the invention, there is provided as a novel microorganism, a transformed cell of *Escherichia coli*, characterized in that the cell carries therein such a recombinant plasmid which has been prepared by ligating a DNA fragment containing therein the DNA sequence shown in SEQ ID No. 1 of Sequence Listing, to the restriction endonuclease EcoRI cleavage site of the plasmid vector pBluescript II SK(+) with using a DNA ligation kit, and wherein the transformed cell of *Escherichia coli* can proliferate stably in the presence of ampicillin.

The transformed cell of *Escherichia coli* according to the sixth aspect of the invention may be the cell of *Escherichia coli* DAP8-1 strain which is deposited as under Accession No. FERM BP-6310 in terms of the Budapest Treaty at the National Institute of Bioscience and Human-Technology, the Agency of Industrial Science and Technology, in Japan.

Various diverse kinds of plants can be transformed by using, as an exogenous gene, the DNA of the first aspect of the invention or the DNA of the second aspect of the invention. The method for inserting the inventive DNA as the exogenous gene into a plant for plant transformation may be any of various biotechnology methods which are conventionally known for that purpose.

Next, a method, which can be worked suitably for inserting the DNA of the first aspect of the invention or the DNA of the second aspect of the invention as an exogenous gene into the rice plant, is summarily described herein below. This method is illustrated in Example 4 hereinafter.

(1) Preparation of a Recombinant Vector for Insertion of Exogenous Gene

When the known plasmid vector pBI221 (manufactured by Clontech, Co.) comprising the 35S promoter of cauliflower mosaic virus and the NOS terminator and an ampicillin-resistant gene is treated with restriction endonucleases XbaI and SacI in a buffer, there can be produced such a vector DNA fragment of about 3.8-kb length which is cut at the XbaI cleavage site located at downstream of the 35S promoter and which is cut at the SacI cleavage site located at upstream of the NOS terminator present in said plasmid vector.

An aqueous solution of said vector DNA fragment of about 3.8 kb is mixed with an aqueous solution of the DNA of this invention, and the resulting mixture is subjected to a ligation reaction by treating the mixture with a DNA ligation kit. Thereby, there can be produced such a recombinant vector, wherein the DNA of this invention is inserted and ligated at the position between the 35S promoter region and the NOS terminator region of said vector DNA fragment.

The recombinant vector so produced is then integrated in *Escherichia coli* XL1-Blue MRF', to prepare the transformant cells of *Escherichia coli*.

The resulting transformed cells of *Escherichia coli* are inoculated to and cultured in a culture medium containing an antibiotic, ampicillin, to afford a number of colonies of *Escherichia coli* which are resistant to ampicillin. Furthermore, these colonies are separately cultured and proliferated in further volumes of the culture media containing ampicillin.

From the ampicillin-resistant *Escherichia coli* cells as proliferated in the individual bacteria colonies, then, there are separately harvested the plasmids. The so harvested plasmids are composed of various plasmids wherein the DNAs as inserted are linked with each other in variable directions. The various plasmids as harvested from each bacteria colony are then digested with restriction endonucleases XbaI and SacI. The resultant digestion solution containing the various digested DNA fragments is further subjected to agarose gel electrophoresis. By the analysis of the lengths and the nucleotide sequences of these digested DNA fragments, it is possible to select an appropriate recombinant plasmid (of a size of about 4.9 kb) wherein the DNA of this invention has been inserted and ligated in the normal orientation at the downstream of the 35S promoter present in the recombinant vector.

The so selected recombinant vector carrying therein the DNA of the first aspect of the invention, which has been inserted and ligated therein in the normal orientation, is now referred to as "vector pDAP". The so selected recombinant vector carrying therein the modified DNA-158N fragment of the second aspect of the invention, which has been inserted and ligated in the normal orientation therein, is now referred to as "vector p158N". Additionally, the recombinant vector carrying therein the modified DNA-166A fragment of the second aspect of the invention, which has been inserted and ligated therein in the normal orientation, is now referred to as "vector p166A". All these selected recombinant vectors contain one of the DNA fragments of this invention as well as the 35S promoter region, the NOS terminator region and the ampicillin-resistant gene (Am$^r$).

(2) Preparation of Rice Callus

From the completely ripe rice seeds are removed the outer grain shells. The resulting hulled rice seeds having outer skin are sterilized in an aqueous ethanol solution and then in a dilute aqueous solution of sodium hypochlorite, and are rinsed with sterile water.

The sterilized and rinsed rice seeds having outer skin are then placed in a callus-forming MS culture medium having been supplemented with sugar, a plant hormone, 2,4-PA and agar. Rice calluses are formed when the rice seeds are then cultured at 28° C. under irradiation of sun-light at 1500 to 2500 lux for 15 to 18 hours per day for consecutive 40 to 50 days. The calluses are cut out and separated from the albumen part of each rice seed, and then sieved to afford calluses each of a dimension of 1 mm or less.

(3) Preparation of Whiskers for Transfer of Gene

A great number of a commercially available whiskers (microfine needle-like bodies) made of potassium titanate is placed and sterilized in ethanol within a small tubular container. The ethanol is then absolutely removed from the container through evaporation. Sterile water is placed in the tubular container containing the sterilized whiskers therein, in order to rinse the whiskers. The wash liquor is then removed by centrifugation. To the tubular container containing therein the rinsed whiskers, there is added a liquid R2 medium, thereby to prepare a suspension of the whiskers.

(4) Preparation of Materials for Introduction of Exogenous or Foreign Gene in the Rice Callus Cell The above-mentioned recombinant vector (namely, the vector pDAP, the vector p158N or the vector p166A) carrying the DNA of this invention as normally inserted and ligated therein, which has been prepared as described above in the item (1), is dissolved in a TE buffer, thereby to prepare a solution of the recombinant vector.

In the said tubular container containing therein the above whiskers suspension are then placed and charged said calluses of a dimension of 1 mm or less. The charged amount of the whiskers is adjusted to 1 to 100 mg per 1 ml of PCV (Packed Cell Volume) of the callus. The resultant mixture present in the container is then agitated and centrifuged. The resulting supernatant is discarded, and a mixture of the rice callus cells with the whiskers is thus obtained as the precipitate.

To said precipitate which is composed of the mixture of the callus cells and the whiskers, there are added a solution of the recombinant vector carrying the DNA of this invention (namely, the vector pDAP, the vector p158N or the vector p166A) and a solution of the known plasmid vector p35SC-SS containing therein a gene resistant to a herbicide phosphinothricin as a selection marker. The resultant admixture is then sufficiently shaked. In this manner, a homogenous mixture which is comprising the callus cells, the whiskers, the recombinant vector carrying the DNA of this invention and the plasmid vector p35SC-SS, can be prepared. The homogeneous mixture is then repeatedly subjected to a series of centrifugation and shaking, thereby to prepare the mixture which has been made more homogenous.

(5) Manipulation of Exogenous Gene for Insertion of the Gene into Rice Callus

The above-mentioned homogenous mixture comprising the callus cells, the whiskers, the recombinant vector carrying the DNA of this invention and the plasmid vector p35SC-SS, which has been prepared as above in the item (4), is then treated by ultrasonic irradiation. The irradiating ultrasonic wave may be of a frequence of 10 to 60 kHz, and the irradiation intensity may be 0.1 to 1 W/cm². By effecting the ultrasonic treatment of said homogeneous mixture for 30 seconds to 2 minutes, the recombinant vector which is carrying the DNA of this invention and the plasmid vector serving as the selection marker, can be introduced, with aid of the physical ultrasonic action and the whisker's action, into the callus cells which are to be integrated with the DNA of this invention.

(6) Selection of Callus Cells as Transformed with the Introduced Recombinant Vector The mixture which has ultrasonically been treated as described in the above, is then rinsed with R2 liquid culture medium. The resulting rinsed mixture is centrifuged to isolate the callus cells from the whiskers. The so isolated callus cells are the transformant cells, wherein the introduced plasmid vector has been carried therein.

The resultant callus cells carrying the introduced plasmid vector are plated on a plant cell-incubating medium which was prepared by adding sucrose and a plant hormone 2,4-PA to the routine R2 medium. The callus cells are incubated at 27 to 29° C. under shaking and irradiation of light at 1,500 to 2,000 lux for 15 to 20 hours per day. Thereby, the callus cells can proliferate by occurrence of the cell division.

After incubation for 2–3 day, the resulting suspension of the thus differentiated plant cells is spread evenly on a selecting medium which essentially comprises an N6 medium as supplemented with sucrose, 2,4-PA, Gelrite and a herbicide, phosphinothricin. Then, the plant cells are incubated at 27 to 28° C. under irradiation of light at 1500 to 2000 lux for 15 to 20 hours per day for consecutive 25 to 30 days. In this way, there can be prepared the phosphinothricin-resistant plant cells which has been transformed with the introduced vector.

(7) Re-selection of Transgenic Plant Cells

From among the phosphinothricin-resistant transgenic plant cells obtained as above, there are re-selected and separated only the transgenic plant cells containing a sufficient amount of the DNA of this invention as the exogenous gene therein.

For this purpose, the above transformed plant cells are transplanted on a re-selecting medium which essentially comprises an N6 medium as supplemented with sucrose, 2,4-PA, Gelrite and a lysine-analog, AEC [namely, S-(2-aminoethyl) cysteine].

The plant cells on the re-selecting medium are cultured at 27 to 28° C. under irradiation of light at 1,800 to 2,000 lux for 15 to 16 hours per day, for 25 to 30 days.

The transgenic plant cells containing the sufficient amount of the DNA of this invention as the exogenous gene is able to grow even in the presence of AEC having a cell proliferation-inhibiting activity which is contained in the re-selecting medium, because said transgenic plant cells are resistant to AEC. The AEC-resistant plant cells which could grow and were cultured in the above re-selecting medium containing AEC added, are then selected and separated.

(8) Regeneration of a Plant from the AEC-resistant Transgenic Plant Cells as Re-selected The AEC-resistant transgenic plant cells which have thus been re-selected are then transplanted onto a differentiating medium for regeneration of plant body, which culture medium comprises the MS medium for cultivation of plant tissue and has been supplemented with sucrose, benzyladenine and naphthalene acetate, as plant hormone, and Gelrite.

The plant cells as transplanted on the differentiating medium are cultured at 27 to 28° C. under irradiation of light at 1,800 to 2,000 lux for 15 to 16 hours per day, for 25 to 30 days. The so cultured transgenic plant cells have been differentiated, to regenerate the bud and root of the plant.

After the plumules having the regenerated bud and root have grown to a length of 10 to 30 mm, the plumules are transplanted onto to an acclimating medium which essentially comprises an MS medium as supplemented with sucrose and Gelrite. The plumules as transplanted are incubated on the acclimating medium at 27 to 28° C. under irradiation of light at 1,800 to 2,000 lux for 15 to 16 hours per day, for consecutive 18 to 20 days.

In this manner, a transgenic plant can be regenerated. The resulting body of the transgenic plant is transplanted in soil and then cultivated under normal conditions in a green house, to allow the plant to grow normally and to fructify rice seed by cultivation for 3 to 6 months.

(9) Verification of the Exogenous Gene as Introduced

Green leaves are harvested from the regenerated body of the transgenic rice plant so obtained. The harvested leaves are frozen in liquid nitrogen and then disrupted. From the disrupted pieces of the leaves is then extracted the DNA according to the method of J. Sambrook et al., (described in the Molecular Cloning, 2-nd edition, Cold Spring Harbor Laboratory Press, 1989).

Further, an oligonucleotide of the nucleotide sequence of SEQ ID No. 14 of Sequence Listing, as well as an oligonucleotide of the nucleotide sequence of SEQ ID No. 15 are chemically synthesized to be used as the primers.

The DNA as extracted from the regenerated body of the transgenic rice plant is used as the template and the above-mentioned two types of the synthetic oligonucleotides are used as primers, to carry out the PCR method, whereby said DNA can be amplified according to the known PCR method. The resulting amplification solution is then fractionated by agarose electrophoresis in a conventional manner. Then, there is separated and collected such a gel band carrying only the DNA fragment which is corresponding to the DNA of said introduced exogenous gene but which is presented among the various DNA fragments of the DNA as extracted from said regenerated transgenic rice plant.

By making Southern analysis of the nucleotide sequence of the DNA fragment which is contained in the so collected gel band, it can be identified whether said DNA fragment is corresponding to the DNA of this invention.

In the foregoing descriptions, there has been described a preferable method for transforming the rice plant which comprises introducing the DNA of this invention as an exogenous gene into the rice plant. While, the DNA of this invention may also be used for the transformation of other plant species, by introduction of the DNA of this invention not only in rice plant but also in other plant species. Accordingly, a method for introduction of the DNA of this invention into the body of a plant will be described in general hereinbelow.

The plants in which the DNA of this invention may be introduced, include, for example, rice, corn, wheat, barley, and other monocots, as well as dicots such as tobacco, soy bean, cotton, tomato, Chinese cabbage, cucumber and lettuce, but are not limited thereto. It is advantageous that cultured cells are at first prepared from one of these plants, and the DNA of this invention is introduced as an exogenous gene into the resulting cultured cells.

The preparation of the cultured cells for use in the introduction of the DNA of this invention may be done with employing any of explant as derived from plant, which may be, for example, such explant as derived from scutellum, meristem, pollen, anther, lamina, stem, petiole and root of the plant.

It is advantageous that the explant as above is placed and incubated on a medium for forming callus, which may be for example such a medium that is prepared by admixing a plant tissue-incubating medium comprising inorganic components and vitamins as the essential components, with a plant hormone such as 2,4-PA (2,4-dichlorophehoxyacetic acid) in an amount of 0.1 to 5 mg/liter and carbon sources such as sucrose in an amount of 10 to 60 g/liter and Gelrite in an amount of 1 to 5 g/liter. Said plant tissue-incubating medium may be the MS medium (Murashige et al., Physiological Plantarum, Vol. 15, pp. 473–497, 1962), or the R2 medium (Ojima et al., Plant and Cell Physiology, Vol. 14, pp. 1113–1121, 1973), or the N6 medium (Chu et al., In Proc. Symp. Plant Tissue Culture, Science Press Peking, pp. 43–50, 1978). The resulting cells as cultured in the above manner may then be used for the introduction of the DNA of this invention thereinto.

The plant cells into which the DNA of this invention may be introduced are preferably, for example, dedifferentiated cultured cells such as callus and suspended cells thereof, or cultured cells made of adventitious embryo and shoot primordium, or callus cells or suspended cells thereof as prepared from the cells of plant tissues such as leaf, root, stem, embryo and meristem of the plant.

To prepare the cultured cells for use in the introduction of the DNA of this invention thereinto an explant piece may be placed and incubated on a callus-forming medium. In this case, the incubation period which is required for the formation of the cultured cells for use in the introduction of the DNA of this invention into said cultured cells is not specifically limited. However, it is essential to regenerate the resulting transgenic plant, and hence it is important to employ such cultured cells which are capable of producing the regenerated plant from the cultured cells, and which are namely cultured cells as harvested within the period of time during which the cultured plant cells can still retain their ability to regenerate the plant therefrom.

The cultured cells for use in the introduction of the DNA of this invention therein may be in the form of any suspended cells which are obtained by culturing the cells in a liquid medium, so long as the cultured cells as suspended are retaining the ability to regenerate the plant.

In order to introduce the inventive DNA (namely, the DNA of this invention) in a plant cell, it is at first necessary to prepare such a recombinant vector in which the inventive DNA has been inserted in an expressing vector. The recombinant vector so prepared is necessary to be such a recombinant vector which is so constructed and arranged that the inventive DNA is located at downstream of the expressing promotor in the recombinant vector and a terminator is located downstream of the inventive DNA, whereby the inserted DNA can be made to express in the transformed plant after the introduction of the DNA into the plant. Depending on the type of a method as employed for the introduction of DNA in plants, the recombinant vector which is to be used for that purpose may be any of the various vectors which have usually been utilized in routine transformation of plants. For example, it is convenient to employ such plasmid vectors which are capable of proliferating in the cell of *Escherichia coli*, such as ones of pUC series and pBR322 series in cases when there are used direct methods for the introduction of DNA in plant cells, which are operable by electroporation process, particle gun process and whisker process. While, it is convenient to employ such plasmid vectors such as one of plan series is a case when there is used the Agrobacterium process.

The promoters which is to be located at upstream of the inventive DNA within in said recombinant vector include, for example, CaMV35S as derived from cauliflower mosaic virus [see The EMBO Journal, Vol. 6, pp. 3901–3907, 1987; or JP-A-6-315381]; ubiquitin promoter as derived from corn [JP-A-2-79983]; and phaseolin promoter [see Plant Cell, Vol. 1, pp. 839–853, 1989]. Further, the terminator which is to be located at downstream of the inventive DNA within the said recombinant vector may be, for example, the terminator as derived from cauliflower mosaic virus, or the terminator as derived from nopaline synthase gene [see The EMBO Journal, Vol. 6, pp. 3901–3907, 1987]. However, any promoter or terminator which is capable of functioning in plants may satisfactorily be used.

In order to enable it to efficiently select the plant cells which have been transformed by the introduction of the inventive DNA therein, it is preferable that the recombinant vector for use therefor is introduced into the plant cells, along with a plasmid vector which is containing a gene useful as an appropriate selection marker. For this purpose, as the selection marker gene is used either a hygromycin phosphotransferase gene which is resistant to an antibiotic hygromycin, or a neomycin phosphotransferase gene which is resistant to kanamycin and gentamycin, or an acetyltransferase gene which resistant to a herbicide, phosphinothricin [see The EMBO Journal, Vol. 6, pp. 2513–2518, 1987; or JP-A-2-171188].

The methods which may be used for the introduction of the inventive DNA as the exogenous gene into a plant, may include the Agrobacterium process [Bio/technology, Vol. 6, pp. 915–922, 1988], electroporation process [Plant Cell Rep., Vol. 10, pp. 106–110, 1991]; particle gun process [Theor. Appl. Genet., Vol. 79, pp. 337–341, 1990]; and whisker method, but to which this invention is not limited.

According to the whisker method for the introduction of the inventive DNA as the exogenous gene into the plant, the whiskers suitably usable may specifically be of a diameter of 0.01 to 10 $\mu$m, preferably 0.5 to 1 $\mu$m and of a length of 1 to 100 $\mu$m, preferably 3 to 40 $\mu$m. The whiskers may be made of a material such as potassium titanate, calcium carbonate, aluminium borate, silicate nitride, zinc oxide, basic magnesium sulfate, magnesia, magnesium borate, carbon graphite, calcium sulfate, sapphire, and silicon carbide. The whisker is preferably made of potassium titanate, calcium carbonate, or aluminium borate.

The whisker having received no surface treatment can here be used as such. However, the rate of the transformation of plant cells can be raised when use is made of a whisker having been treated so as to confer basic functional groups on the surface of the whisker, or preferably a whisker having the surface treated with a surface-treating agent.

Any of a compound capable of forming a covalent bond with the whisker surface may satisfactorily be used as the treating compound which can confer the basic functional groups to the whisker surface. The compound usable for this purpose is preferably a silane coupling agent, more preferably a silane coupling agent having a basic functional group. As the silane coupling agent, use can be made of a basic, silane coupling agent such as 3-(2-aminoethoxyaminopropyl)-trimethoxysilane and 3-aminopropyl-triethoxysilane. Any silane coupling agent having the basic functional group can satisfactorily be used.

An appropriately adjusted quantity of the plant cells is mixed with the whiskers at first in a liquid medium. The volume of the plant cells to be mixed with the whiskers is not limited to a specific value. The volume of the whiskers to be mixed into a liquid medium, along with the plant cells, may be adjusted, depending on the volume of the plant cells. Per 1 ml of PCV for the plant cells, the whiskers may be added in an amount of 1 to 100 mg, preferably 4 to 40 mg.

In this way, a mixture of the plant cells, the whiskers and the recombinant vector carrying therein the inventive DNA as dispersed in the liquid medium is prepared. The mixture is then centrifuged. For example, said mixture may be centrifuged at a centrifugal accelerated rate of 3,000 to 50,000×g, preferably 10,000 to 30,000×g for 10 seconds to 40 minutes, preferably 5 to 10 minutes. Thereafter, the resulting precipitate is subjected to the ultrasonic treatment. For example, the ultrasonic treatment may comprise the irradiation of ultrasonic wave at a frequency of 1 k to 1 MHz, prefer-ably 10 to 60 kHz and at an intensity of 0.01 to 10 W/cm$^2{}_1$ preferably 0.1 to W/cm$^2$ for an irradiation period of 0.2 second to 20 minutes, preferably 30 seconds to 2 minutes.

From the mixture having received the ultrasonic treatment, there are separated the plant cells by centrifugation. The so harvested plant cells contain the recombinant vector carrying therein the inserted inventive DNA, as well as the plasmid vector usable as the selection marker.

The thus harvested plant cells which are carrying the exogenous gene as introduced therein, are then rinsed in a liquid medium. Thereafter, the plant cells are plated and cultured in a known selecting medium which contains an appropriate, selecting chemical agent varying depending on the type of the selection marker gene as integrated in the plant cells. Thereby, the cultured transgenic plant cells can be prepared.

In order to re-select the transformed plant cells which contain the recombinant vector carrying the inventive DNA therein in a sufficiently effective amount of the vector, said transformed plant cells are then cultured in a re-selecting medium containing lysine analog added as a cell proliferation-inhibiting agent. As the lysine-analog, S-(2-aminoethyl)-cysteine (AEC) or O-(2-aminoethyl)-serine, for example, may be added at a concentration of 10 mg/liter to 1000 mg/liter, preferably 100 mg/liter to 300 mg/liter to the re-selecting medium.

The transformed plant cells which are carrying the recombinant vector containing the inserted inventive DNA and are carrying the vector as the selection marker, may be re-selected in this manner, and are then incubated to regenerate the plant therefrom. The plant can be regenerated according to a known technique. For example, the plant can be regenerated by plating and incubating the above, re-selected transformed plant cells in a known medium which is conventional for the plant regeneration.

The above, re-selected transformed plant cells are thus plated in the medium for the plant regeneration and may then be incubated therein at a temperature of 15 to 30° C., preferably 20 to 28° C., under irradiation of light at 500 to 2,000 lux, preferably 800 to 1,000 lux for an incubating period of 20 to 60 days, preferably 30 to 40 days.

Thereby, from the so incubated individual plant cells can be regenerated the bodies of the transformed plant in which the recombinant vector carrying therein the exogenous gene containing the inventive DNA has been introduced.

The resulting plant as regenerated from said transformed plant cells is then cultivated in an acclimation medium. Thereafter, the so acclimated, regenerated plant is cultivated under normal cultivation conditions in a greenhouse. By the cultivation of the plant for 3 to 6 months, the plant reaches its mature stage to fructify seeds, which can be harvested.

The presence of said exogenous gene which is introduced in the transgenic plant as regenerated and cultivated in the above manner, can be confirmed by effecting the analysis of the nucleotide sequence of the DNA present in said plant according to known PCR method and Southern method [Southern, J. Mo. Biol., Vol. 98, pp. 503–517, 1975].

In this case, extraction of the DNA from said transqenic plant may be practiced according to the known method of J. Sambrook [Molecular Cloning, 2-nd edition, Cold Spring Harbor Laboratory Press, 1989].

When there is conducted by PCR method the analysis of the inventive DNA present as the exogenous gene in the regenerated transgenic plant, the DNA as extracted from the regenerated transgenic plant is used as template, and further, synthetic oligonucleotides having the nucleotide sequences as appropriately chosen depending on the DNA of the first aspect of the invention or the modified DNA of the second aspect of the invention are used as primers, and then they together are added to a reaction mixture for PCR method to carry out the amplification reactions of DNA. The amplification reactions for this purpose comprise repeating the modification of the DNA and the annealing and extension of DNA by several tens of times, so that an amplified product of the DNA fragment containing the DNA sequence of this invention can be produced.

The resultant amplification reaction solution containing said amplified product may then be subjected, for example, agarose gel electrophoresis in order to fractionate the various amplified DNA fragments so produced. An agarose gel band which carries the DNA fragment containing therein the DNA sequence corresponding to the DNA of this invention as the integrated exogenous gene is then cut out and separated from the agarose gel. By making Southern analysis of the nucleotide sequence, it can be determined whether or not the nucleotide sequence of the DNA fragment contained in the gel band thus cut out and separated is corresponding to the DNA of this invention.

In a seventh aspect of the invention, there is further provided a recombinant vector as prepared by insertion of a DNA fragment carrying therein the DNA sequence of 1143 bp shown in SEQ ID No. 1 or No. 5 or No. 7 of Sequence Listing, into such a plasmid vector which comprises a cauliflower mosaic virus-derived promotor capable of expressing in a plant, as well as the NOS terminator and an ampicillin-resistant gene, and wherein, in the recombinant vector, the inserted DNA sequence of 1143 bp is located so as to be controllable by said promoter.

The plasmid vector mentioned just above is preferably the aforesaid plasmid vector pBI221.

PREFERRED EMBODIMENTS OF THE INVENTION

Figure 1:
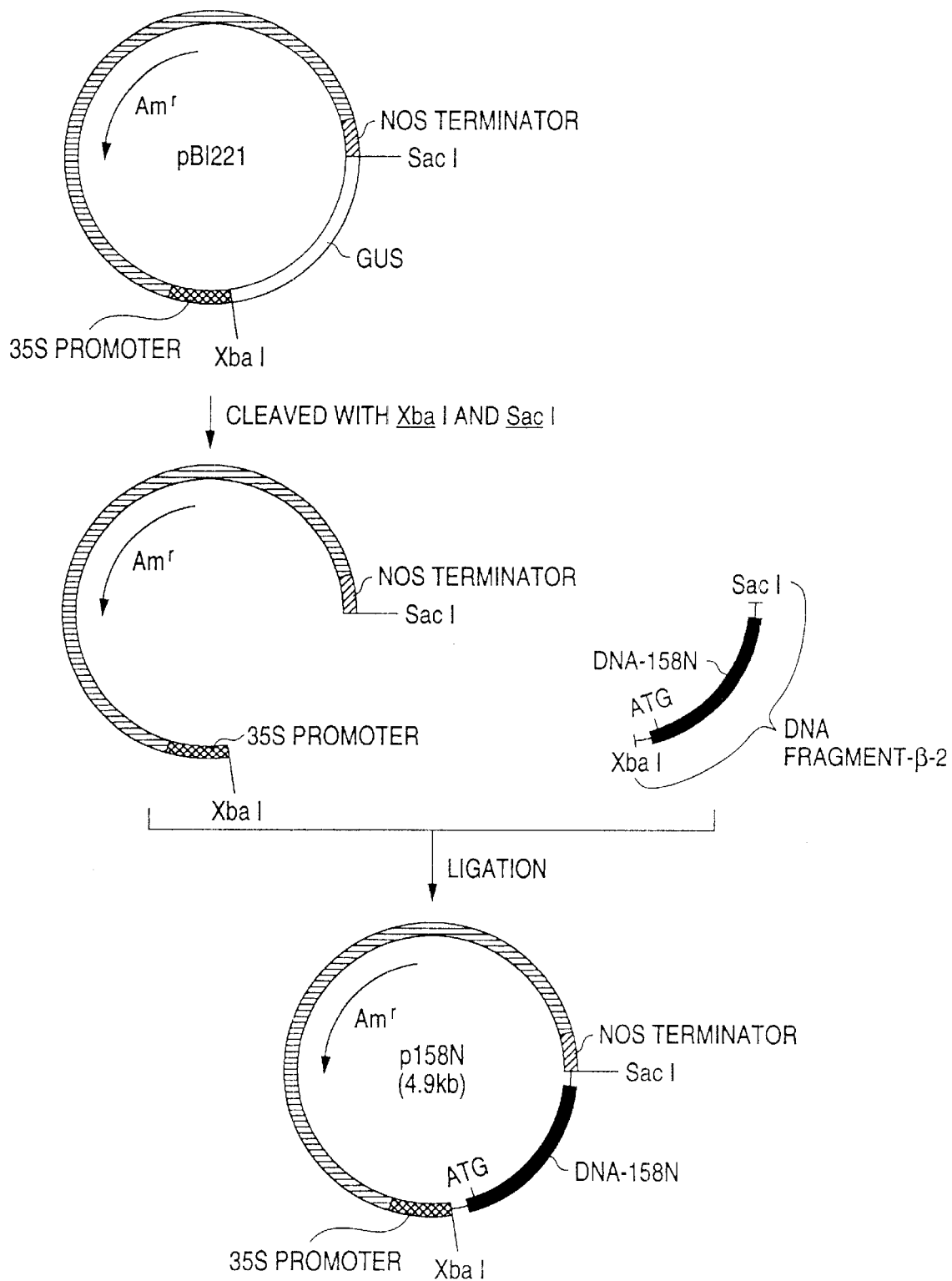
FIG. 1 shows diagrammatically a flow chart of depicting the procedures for preparing from the vector pBI221, the aforesaid vector p158N which is a recombinant vector useful for the introduction of an exogenous gene to be used for the transformation of cultured cells of rice in Example 4 hereinafter, and which carries therein the modified DNA-158N sequence according to the second aspect of this invention.
Figure 2:
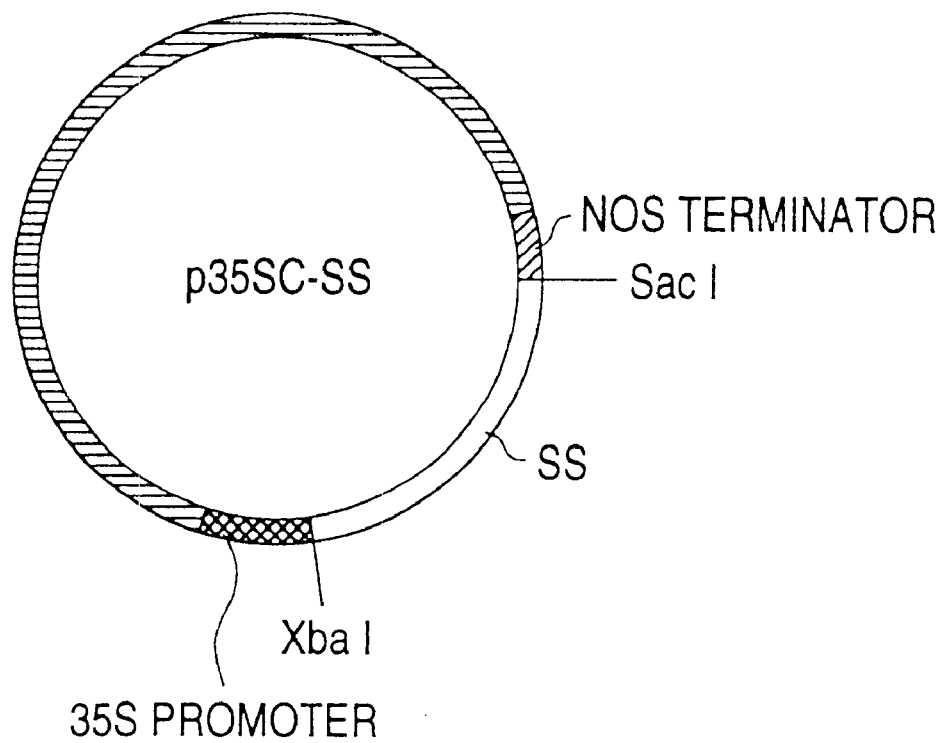
FIG. 2 depicts diagrammatically the structure of the vector p35SC-SS which contains the phosphinothricin gene SS as the selection marker and which may be introduced, along with the vector p158N, into the cultured cells of rice, in Example 4 hereinafter.

Next, the first aspect of this invention is illustrated with reference to Example 1 which illustrates the preparation of a DNA fragment carrying the rein the DNA sequence of 1143 bp according to the first aspect of the invention (that is, the DNA sequence of the nucleotide sequence shown in SEQ ID No. 1 of Sequence Listing, namely the DHDPS-DNA-1143 sequence). Further, the second aspect of the invention will be illustrated with reference to Example 2 which illustrates the preparation of a DNA fragment carrying therein the modified DNA-158N sequence of 1143 bp according to the second aspect of the invention (that is, the DNA sequence of the nucleotide sequence shown in of SEQ ID No. 5 of Sequence Listing), as well as and with reference to Example 3 which illustrates the preparation of a DNA fragment carrying therein the modified DNA-166A sequence of 1143 bp according to the second aspect of the invention (that is, the DNA sequence of the nucleotide sequence shown in SEQ ID No. 7 of Sequence Listing).

Furthermore, the third aspect of this invention is illustrated with reference to Example 4 which illustrates the method for transforming a rice plant by introduction of the DNA of this invention as inserted in the recombinant vector, as an exogenous gene, into the rice plant.

The procedures for the experimental manipulation as described in the following Examples are those which are carried out according to the methods described in the Molecular Cloning, 2-nd edition, J. Sambrook et al., Cold Spring Harbor Laboratory Press (1989), unless otherwise stated.

EXAMPLE 1

(1) Preparation of Rice mRNA

Seeds of rice plant (variety: Nippon-bare) were sown. On day 7 of the cultivation, 2 g of the stems and leaves of the young rice plants was frozen in liquid nitrogen. The frozen stems and leaves were disrupted in a mortar. From the disrupted plant material so obtained was extracted a total RNA of about 2 mg, according to the known AGPC method (the method using acid guanidinium thiocyanate phenol-chloroform) (Experimental Medicine, Vol. 9, No. 15 (November issue), pp. 99–102, 1991). Then, mRNA was isolated from the resulting total RNA by means of an mRNA purification kit (mRNA Purification Kit; manufactured by Pharmacia Biotech, Co., Ltd.). In this manner, the mRNA of rice was obtained at a yield of about 30 μg.

(2) Construction of Rice cDNA Library

From the mRNA as obtained in (1) above were produced cDNAs by means of a cDNA synthesis kit (Time Saver cDNA Synthesis Kit; manufactured by Pharmacia Biotech, Co. Ltd.).

The resultant cDNAs were linked to a phage vector λgt11, of which the EcoRI cleavage terminus had been treated with the calf intestine-derived alkaline phosphatase [see DNA Cloning Techniques, IRL Press, Oxford, Vol. 49, 1985; Lamda gt11/EcoRI/ClAP-treated Vector Kit; manufactured by STRATAGENE CO.). Then, the resulting recombinant vectors were packaged in the λ phage by using an in vitro packaging kit [Gigapack II Gold Packaging Extract; manufactured by STRATAGENE LTD.].

*Escherichia coli* Y1088 was then infected with the thus produced recombinant phage and then proliferated. A great number of said recombinant phages was produced as plaques of the lysogenized cells of *Escherichia coli*. The recombinant phages present in the plaques comprised a variety of the recombinant phages containing therein the inserted cDNAs derived from rice, and these recombinant phages were used as a rice cDNA library.

(3) Construction of Primers for PCR Method

For the purpose of preparing such a DNA probe for PCR method, which serves for cloning of the cDNA fragment to encode the rice DHDPS, a primer was designed at first. For this purpose, and also with reference to the known nucleotide sequences of the DHDPS genes of wheat and corn and with reference to the known DHDPS amino acid sequences of DHDPS, the following two types of oligonucleotides were prepared as primers No. 1 and No. 2.

Primer No. 1 (having the nucleotide sequence of SEQ ID No. 3 of Sequence Listing):

5'-GTAATAGTTGGAGGAACAACAGGAG-3'

Primer No. 2 (having the nucleotide sequence of SEQ ID No. 4 of Sequence Listing):

5'-GAGCTGAGCCAGAGCAGTGTTGAG-3'

The aforementioned two oligonucleotides were synthetized by using a DNA synthesizer (Model 391; manufactured by Applied Biosystems, Co. Ltd.) and purifying with ion exchange HPLC.

(4) Preparation of Probe DNA

The above-mentioned two types of the oligonucleotides were used in an amount of 10 p.M each as the first primer and second primer, respectively. The rice cDNA library comprising the recombinant phages which were produced above in (2), was used as the template. These primers and template together were added to 50 μl of an amplification mixture for PCR [comprising 10 mM Tris-HCl, pH 8.3, 1.5 mM $MgCl_2$, 50 mM KCl, 0.001% gelatin, pH 8.3, and a mixture of 4 dNTPs each at 2.5 mM, and a DNA polymerase TaKaRa Ex Taq of 2.5 units], to effect amplification of DNA. The amplification mixture here used had been prepared by using a PCR kit (PCR Amplification Kit; manufactured by TaKaRa Brewery Co., Ltd.).

The amplification reaction of the DNA by PCR method was effected by repeating 35 times a reaction cycle which consisted of three reactions, namely denaturation at 94° C. for 30 seconds, annealing at 55° C. for one minute, and extension at 72° C. for 2 minutes, with using a pCR reaction apparatus (DNA Termal Cycler 480, manufactured by PERKIN ELMER).

Thus, the amplification products of the DNA fragments which constitute parts of the DNA sequence corresponding to the rice DHDPS gene were produced. And, these DNA fragments were then collected as the probe DNAs. These probe DNAs were used for the following procedure of cloning the cDNA library.

(5) Selection of DNA of the Rice DHDPS Gene from the Rice cDNA Library

From the recombinant phages present in the rice cDNA library as prepared in (2) above, there were selected by screening the recombinant phares having contained the inserted DNA sequence corresponding to the rice DHDPS gene, with the selection being made by using the probe DNAS as prepared above in (3).

For that purpose, the aforesaid plaques comprising the recombinant phages which are the rice cDNA library as produced above in (2), were provided by being formed on a 1.5% agar medium. These plaques on the agar medium were then transferred onto a nylon membrane, High Bond N(manufactured by Amersham, Co.). The phage DNAs which were contained in the phage plaques as transferred onto the nylon membrane, were treated with an alkaline denaturation mixture (comprising 1.5 M NaCl, 2.0 M NaOH) for 10 minutes, and with a neutralization mixture (comprising 1.0 M Tris-HCl, pH 5, 2.0 M NaCl) for 10 minutes, followed by treating with UV irradiation, so as to immobilize the DNAs on the nylon membrane.

Next, the probe DNAs so produced above in (4) were labeled with digoxigenin (DIG), to prepare a labeled probe DNAs. The labeled probe DNAs were then plaquehybridized to said nylon membrane having said phage DNAs immobilized thereon. The labeled probe DNAs were prepared by using DIG-ELISA DNA Labeling & Detection Kit (manufactured by Boehringer Mannheim, CO.).

In the above case, said nylon membrane having the phage DNAs immobilized thereon was immersed in a hybridization mixture (comprising 500 mM Na-Pi buffer, pH 7.2, 7% SDS, 1 mM EDTA) at 65° C. for 10 minutes. Then, said labeled probe DNAs of 10 ng/ml were added to the hybridization mixture containing the nylon membrane therein, followed by effecting the hybridization reaction at 65° C. for 15 hours.

After the termination of the hybridization reaction, the nylon membrane having the resulting hybridization products was rinsed with a rinsing solution (comprising 40 mM Na-Pi buffer, pH 7.2, 1% SDS) for 20 minutes. The rinsing procedure was repeated three times. Thereafter, the DIG-ELISA Labeling & Detection Kit was used to detect the desired recombinant phage. Four plaques of such recombinant phages which emitted intense signals on an X-ray film due to having received the hybridization, and which are the recombinant phages presumably carrying therein the integrated DHDPS gene, could thus be detected in among the 300,000 phage plaques. Then, the above, four plaques of the recombinant phages could be selected and isolated.

From each of these four recombinant phage plaques so selected, there was isolated the λ DNA by means of a λ DNA isolation kit (λ DNA Purification Kit; manufactured by STRATAGENE, LTD.).

The above isolation of λ DNA was made by the following procedures. Thus, 20 mg/ml DNase I (50 µl) and 2 mg/ml RNase A (200 µl) were added to a liquid culture in which a vast amount of each recombinant phage as selected had been proliferated. The resulting mixture was left to stand at ambient temperature for 15 minutes. The resulting culture broth containing the proliferated phages was centrifuged at 15,000 rpm at 4° C. for 10 minutes. To the resulting supernatant was added 25 ml of 80% DEAE-cellulose, followed by incubation at ambient temperature for 10 minutes. The resulting incubated mixture was centrifuged, and the resulting supernatant were added with 2 ml of 0.5 M EDTA and 770 µl of 50 mg/ml Pronase. The resulting reaction mixture was left to stand at 37° C. for 15 minutes, followed by being added with 1.5 ml of a 5% CTAB solution [comprising 1% CTAB (cetyl trimethyl ammonium bromide), 50 mM Tris-HCl, pH 8.0, and 10 mM EDTA]. The resulting mixture was treated by allowing it to stand at 65° C. for 3 minutes and was then left to stand in ice bath for 5 minutes. The respective reaction solutions so prepared were added with a 1/10-fold volume of 3 M sodium acetate and a 2-fold volume of ethanol, and the resulting mixture was left to stand at −20° C. for about 6 hours. Subsequently, the resultant solution was centrifuged, and the precipitated phage DNA was once dried and was then dissolved in 5 ml of water to be stored.

In this way, each of the 4 types of the phage DNAs was isolated. 5 µl of each phage DNA was then digested with 10 units of a restriction endonuclease EcoRI in an H buffer, followed by making the analysis of the resultant digestion mixture. Consequently, it was confirmed that all of the above 4 tyes of the isolated phage DNAs were of one and same DNA sequence.

Accordingly, the DNA fragment which is inserted in the said recombinant phage and is judged to carry the DNA sequence of the rice DHDPS gene, could thus be produced by digesting the phage DNA of the recombinant phage as selected and recovered as above, with the restriction endonuclease EcoRI.

(6) Cloning of cDNA Carrying therein the DNA Sequence Corresponding to the Rice DHDPS Gene The DNA fragment, which was produced as above by digesting from the said recombinant phage, and which was judged to carry the DNA sequence of the rice DHDPS gene, was further inserted in and ligated to the EcoRI cleavage site of a plasmid vector pBluescript II SK(+), by using a DNA ligation kit, so that a recombinant plasmid vector was constructed. *Escherichia coli* XL1-Blue MRF' was transformed then by inserting the so constructed recombinant plasmid vector therein.

The insertion of the so constructed recombinant plasmid vector in *Escherichia coli* XL1-Blue MRF' as described above was conducted by the following procedures. Thus, 10 µl of the recombinant phage DNA produced in the above was digested with 10 units of a restriction endonuclease EcoRI in an H buffer, to prepare a digestion mixture. Separately, 10 µl of the plasmid vector pBluescript II SK (+) was similarly digested with EcoRI, to prepare a digestion mixture. Each of the two digestion mixtures so prepared were added with a 1/10-fold volume of 3 M sodium acetate and a 2-fold volume of ethanol. Each admixture so obtained was left to stand at −20° C. for about 6 hours, and the resulting individual DNA solutions were each centrifuged, to separate and collect the precipitated DNA, which was then dried and dissolved in 5 µl of water. Thus, the aqueous solution of the DNA as derived from the said recombinant phage was obtained, and the aqueous solution of the DNA as derived from the plasmid was obtained. These two aqueous DNA solutions were mixed at each volume of 5 µl together. The resulting mixture was treated with a DNA ligation kit (manufactured by TaKaRa Brewery Co., Ltd.), to ligate the above-mentioned two types of the DNAs with each other. The resulting reaction mixture coming from the DNA-ligation reaction was added with a 1/10-fold volume of 3 M sodium acetate and a 2-fold volume of ethanol. The resulting mixture was left to stand at −20° C. for about 6 hours. The resulting mixture was then centrifuged to precipitate the DNA, which was then separated and dried. The ligated vector DNA so obtained was dissolved in 10 µl of water.

The resultant aqueous solution (10 µl) of the ligated vector DNA (10 ng DNA), as well as commercially available *Escherichia coli* XL1-Blue MRF' competent cells (100 µl; manufactured by STRATAGENE, LTD.) were together placed in a 1.5-ml tube, where the resulting mixture was then incubated for 30 minutes under ice-cooling, then at 42° C. for 30 seconds, and again on ice bath for 2 minutes under ice-cooling. Subsequently, the so incubated mixture was added with 900 µl of an SOC liquid medium (containing 2% Bacto-Tryptone, 0.5% Bacto-yeast extract, 10 mM NaCl, 2.5 mM KCl, 10 mM $MgSO_4$, 10 mM $MgCl_2$, and 20 mM glucose), followed by culturing the *Escherichia coli* at 37° C. for one hour under shaking.

100 µl of the resulting *Escherichia coli* culture was plated on an LB agar medium (containing 1% Bacto-Tryptone, 0.5% Bacto-yeast extract, 0.5% NaCl, 0.1% Glucose, pH 7.5, 1.5% agar) as supplemented with 50 mg/l of ampicillin, 20 mg/l of X-gal (5-bromo-4-chloro-3-indolyl-β-D-galactoside), and 20 mg/l of IPTG (isopropyl-β-D-thiogalactopyranoside). The *Escherichia coli* was incubated therein at 37° C. for 16 hours, and then such *Escherichia coli* colonies as colored white were selected as the *Escherichia coli* which was transformed with the said ligated vector DNA. The white colored colonies were isolated from the *Escherichia coli* colonies which were never colored white.

The so isolated 10 colonies of *Escherichia coli* which are colored white and resistant to ampicillin, were proliferated in a liquid medium containing 50 mg/l ampicillin. From the so further proliferated bacteria of *Escherichia coli* was isolated the plasmid, which was then purified by using a plasmid purification kit (QIA filter plasmid Midi Kit, manufactured by QIAGEN, Co.). By such purification, the plasmid of 50 μg (50 μl) was produced from the transformed *Escherichia coli* cells present in the above ampicillin-resistant bacteria colonies.

The resultant plasmid coloned and produced as above is the desired recombinant plasmid which is a DNA fragment carrying therein the DNA sequence of the rice DHDPS gene and which is of a size of about 4.3 kb.

(7) Analysis of Sequence of the so Cloned DNA

The whole nucleotide sequence of the DNA fragment of the recombinant plasmid (of a size of about 4.3 kb) obtained as the above mentioned cloned DNA fragment can be determined, by treating the recombinant plasmid with a commercially available nucleotide sequencing kit. The nucleotide sequence of the DNA which is corresponding to the rice DHDPS gene and is inserted in the DNA fragment of the aforesaid coloned recombinant plasmid, can be determined, too. The so determined nucleotide sequence of the DNA for encoding the rice DHDPS gene is described in SEQ ID No. 1 of Sequence Listing hereinafter.

Upon making the above determination of the nucleotide sequence of the DNA, the nucleotide sequence of the aforesaid DNA fragment-a was determined by effecting at first a denaturation process by using a sequencing kit (Autoread Sequencing Kit; manufactured by Pharmacia Biotech, Co., Ltd.) and then by effecting the sequencing process with an automatic DNA sequencer [ALF DNA Sequencer II; manufactured by Pharmacia Biotec., Co., Ltd.].

The nucleotide sequence of the DNA which is inserted in the DNA fragment-α as obtained in Example 1 according to this invention and which is judged to encode the rice DHDPS gene, consists of 1140 base pairs present in the single open reading frame set out in the SEQ ID No. 1 of Sequence Listing. The DNA of the nucleotide sequence as shown in SEQ ID No. 1, which is provided in accordance with the first aspect of the invention, encodes a protein consisting of 380 amino acids shown in SEQ ID No. 2 of Sequence Listing. When the amino acid sequence of SEQ ID No. 2 is compared with the amino acid sequence of wheat DHDPS (JP-A-3-127984) and with the amino acid sequence of corn DHDPS (Molecular & General Genetics, Vol. 228, pp. 287–293, 1991), the sequence of SEQ ID No. 2 shows a 82% homology and 79% homology, respectively, to the latter amino acid sequences. Outside the homologous region, the DNA sequence of the first aspect of this invention is obviously different from the known DNA sequences of the DHDPS of wheat and corn. The DNA of the first aspect of the invention therefore has such a DNA sequence which is specific to rice.

EXAMPLE 2

This Example illustrates the preparation of a DNA fragment which carried therein the DNA sequence (namely, a DNA sequence of the nucleotide sequence shown in SEQ ID No. 5 of Sequence Listing) that is designated as the modified DNA-158N sequence and is produced in accordance with the second aspect of the invention.

(1) Construction of Synthetic Oligonucleotide as Primer for PCR Method

A DNA synthesizer (Model-391; manufactured by Applied BioSystems, Co.) was used to construct by chemical synthesis, primer No. 3 which is the oligonucleotide having the nucleotide sequence of SEQ ID No. 9 of Sequence Listing; primer FW-1 having the nucleotide sequence of SEQ ID No. 11; primer RV-1 having the nucleotide sequence of SEQ ID No. 12; and primer BS KPN-1 having the nucleotide sequence of SEQ ID No. 13 of Sequence Listing.

Furthermore, a primer having the nucleotide sequence of SEQ ID No. 14 and a primer having the nucleotide sequence of SEQ ID No. 15 were also synthesized.

(2) Preparation of Template for PCR Method

The DNA fragment as produced by cleavage of the recombinant phage in the item (6) of Example 1 hereinbefore was such the DNA fragment which was judged to carry therein the DNA sequence corresponding to the rice DHDPS gene. Said DNA fragment was now ligated to the EcoRI cleavage site of the plasmid vector pBluescript II SK(+) by means of a DNA ligation kit, to construct a recombinant plasmid vector.

The resulting recombinant plasmid vector pDAP8-1 did contain said DNA fragment inserted therein. In order to render that the sites cleavable by restriction endonucleases XbaI and SacI and usable for PCR are conferred to the said DNA fragment as inserted in the recombinant vector pDAP8-1, the following reactions were carried out.

5 μl of the vector pDAP8-1, as well as 1 μM each of the primer of SEQ ID No. 14 and the primer of SEQ ID No. 15 were added to 100 μl of an amplification mixture [containing 10 mM Tris-HCl, pH 8.3, 1 mM $MgCl_2$, 50 mM KCl, a mixture of 0.2 mM each of 4 dNTPs, and 2.5 units of LA. Taq DNA polymerase], followed by effecting the amplification reaction. The amplification reaction was promoted by repeating 30 times such reaction cycle which consisted of three reaction procedures comprising denaturation at 94° C. for one minute, annealing at 60° C. for 30 seconds, and extension at 72° C. for one minute.

After the termination of the amplification reaction, the amplification reaction solution so obtained was fractionated by low-melting agarose electrophoresis. As the desired, amplified DNA product, there was cut off and separated a band of about 1160 bp, out of the agarose gel. From the so separated band, was produced a purified DNA fragment (XbaI-DNA-SacI)(DNA fragment-XS) which has an XbaI-cleavage site at the 5' terminus and a SacI-cleavage site at the 3' terminus of the DNA sequence for encoding the DHDPS gene, by means of Geneclean II Kit (manufactured by Funakoshi, Co., Ltd.).

Further, 10 μl of a commercially available plasmid vector pUC19 was digested with 10 units of endonuclease XbaI and 10 units of endonuclease SacI in an M buffer.

By using the DNA ligation kit, said DNA fragment (XbaI-DNA-SacI) and the resulting cleaved linear product of the plasmid vector pUC19 were ligated together, so that a cyclic recombinant plasmid vector pDAP8-1-XS (of about 3.9 kb) was prepared.

The plasmid vector pDAP8-1-XS so prepared was then used as the template for the following PCR method.

(3) Amplification by PCR and Recovery of the Required DNA Fragment (i) First Step of PCR Method In order to produce the required DNA fragment by PCR amplification, the following reaction (A) and reaction (B) were conducted as the first step of PCR method.

More specifically, the reaction (A) comprised adding 5 μl of the recombinant plasmid vector pDAP8-1-XS as the template, as well as 1 μM of the primer FW-1, and 1 μM of the primer No. 3 of SEQ ID No. 9 to 100 μl of an amplification mixture [containing 10 mM Tris-HCl, pH 8.3, 1 mM MgCl$_2$, 50 mM KCl, a mixture of 0.2 mM each of 4 dNTPs, and 2.5 units of LA Taq DNA polymerase], followed by effecting the amplification reaction. The amplified DNA product as obtained from the reaction (A) is now referred to as DNA fragment-A.

Furthermore, the reaction (B) comprised adding 5 μl of the recombinant plasmid vector pDAP8-1-XS as the template, as well as 1 μM of the primer RV-1, and 1 μM of the BS KPN-1 to the amplification mixture of the same formulation as in the reaction (A), followed by effecting the amplification. The amplified DNA product as obtained from the reaction (B) is now referred to as DNA fragment-B.

The amplification reaction was made by repeating 30 times a reaction cycle which consisted of three reaction procedures comprising denaturation at 94° C. for 30 seconds, annealing at 55° C. for 2 minutes, and extension at 72° C. for 2 minutes in a PCR reactor [Program Temp Control System PC-700; manufactured by Asthec, Co. Ltd.].

After the termination of the amplification reaction, the amplification reaction mixture coming from the reaction (A) was fractionated by low-melting agarose electrophoresis. Then, a band containing the DNA fragment-A of 480 bp as the amplified DNA product was cut out of the agarose gel. Furthermore, the amplification reaction mixture coming from the reaction (B) was fractionated by low-melting agarose electrophoresis. Then, a band containing the DNA fragment-B of 1200 bp as the amplified DNA product was cut out of the agarose gel.

From these gel bands so cut out, there were respectively separated and produced a purified product of the DNA fragment-A and a purified product of the DNA fragment-B, by using Geneclean II Kit (manufactured by Funakoshi Co., Ltd.).

(ii) Second Step of PCR Method

The second step of the PCR method comprised adding 1 μl of the primer RV-1 and 1 μl of the primer FW-1, and 1 μl each of the DNA fragment-A and DNA fragment-B as amplified individually by the above reactions (A) and (B), respectively, to 100 μl of an amplification mixture [containing 10 mM Tris-HCl, pH 8.3, 1 μM MgCl$_2$, 50 mM KCl, a mixture of 0.2 mM each of 4 dNTPs, and 2.5 units of LA Taq DNA polymerase], followed by effecting the amplification reaction. The amplification reaction was then effected by repeating 20 times a reaction cycle which consisted of three reaction procedures, namely denaturation at 94° C. for 30 seconds, annealing at 55° C. for 2 minutes, and extension at 72° C. for 2 minutes.

After the termination of the amplification reaction, the amplification reaction mixture was fractionated by low-melting agarose electrophoresis. Then, a band containing the desired DNA fragment-C of 1200 bp as the amplified DNA product was cut out of the agarose gel. From the gel band so cut out, there was produced a purified product of the DNA fragment-C, by using Geneclean II Kit (manufactured by Funakoshi Co., Ltd.).

The DNA fragment-C obtained as above is a DNA fragment of about 1350 bp, which carries therein the DNA-158N sequence (of a length of 1143 bp) having the nucleotide sequence of SEQ ID No. 5 of Sequence Listing, and in which a KpnI cleavage site is located at downstream of the 5' terminus of the DNA-158N sequence and an SacI cleavage site is located at upstream of the 3' terminus thereof.

(4) Cloning of DNA Fragment Containing the Modified DNA-158N Sequence

The DNA fragment-C thus produced was then used to prepare a well quantity of a DNA fragment containing the target modified DNA-158N sequence. To this end, the cloning was done according to the following procedures.

(i) 10 μg of the DNA fragment-C produced as above was first digested with 10 units each of restriction endonucleases KpnI and SacI in an L buffer (manufactured by TaKaRa Brewery Co., Ltd.). The DNA fragment as produce by this digestion is now referred to as DNA fragment-β. Further, 10 μg of the pBluescript II SK(+) was digested with 10 units each of KpnI and SacI in an L buffer (manufactured by TaKaRa Brewery Co., Ltd.), to prepare a truncated plasmid. The resultant digestion solution containing the DNA fragment-β, and the resultant digestion solution containing said truncated plasmid were respectively added with a 1/10-fold volume of 3 M sodium acetate and a 2-fold volume of ethanol. The resulting mixtures were individually left to stand at −20° C. for about 6 hours. Thereafter, the resulting individual solutions of DNA were centrifuged, to prepare the precipitated DNA, which was then separated, dried and dissolved in 5 μl of water.

The thus prepared aqueous solution of said DNA fragment-β and the aqueous solution of the truncated plasmid DNA were mixed together at each volume of 5 μl. The resulting mixture (10 μl) was subjected to a ligation reaction by means of a DNA ligation kit (manufactured by TaKaRa Brewery Co., Ltd.), so that the two DNAs as contained in said resulting mixture were ligated with each other. The resulting ligation reaction mixture was added with a 1/10-fold volume of 3 M sodium acetate and a 2-fold volume of ethanol, and the resulting admixture was incubated at −20° C. for about 6 hours. The resulting incubated reaction mixture was centrifuged, to precipitate the DNA, which was then separated and dried. The thus recovered DNA was dissolved in 5 μl of water to prepare an aqueous solution of the DNA.

The DNA, which was present in the resulting aqueous solution so prepared, was a double-stranded recombinant plasmid (the pBluescript-DNA-158N plasmid as described above) which was prepared by ligating the DNA fragment-β with said truncated plasmid as produced by the cleavage of the plasmid vector pBluescript II SK(+) with KpnI and SacI, and in which the modified DNA-158N sequence was contained and was present in the inserted DNA region of said recombinant plasmid.

(ii) Further, *Escherichia coli* XL1-Blue MRF' was transformed by integrating said pBluescript-DNA-158N plasmid therein. Then, the so transformed *Escherichia coli* cells were cultured in a liquid culture medium.

From the cultured cells of the transformed *Escherichia coli* bacteria was extracted a further amount of the plasmid. In this manner, the recombinant plasmid carrying therein the modified DNA-158N sequence could be cloned.

(5) Recovery of DNA Fragment Carrying the Modified DNA-158N Sequence

10 μg of the plasmid DNA of the so obtained pBluescript-DNA-158N plasmid was then digested with 10 units of XbaI and 10 units of SacI in a buffer M (manufactured by TaKaRa Brewery Co., Ltd.). The digestion reaction mixture obtained was fractionated by low-melting agarose electrophoresis. A DNA fragment (referred to as DNA fragment-β-2) which carries therein the DNA-158N sequence (of a length of 1143 bp), was cut out from the agarose gel. The agarose gel band containing the DNA fragment-β-2 was added with an equal volume of a TE buffer (containing 10 mM Tris-HCl, pH 8 and 1 mM EDTA). The resulting mixture was heated at 68° C. for 20 minutes, to dissolve the agarose in the TE buffer. The resulting solution was extracted twice with aqueous saturated phenol, to remove the agarose. The resulting phenol extract containing the DNA was added with a 1/10-fold volume of 3 M sodium acetate and a 2-fold volume of ethanol. The resulting mixture was incubated at −20° C. for about 6 hours. The resulting incubated solution was centrifuged at 15,000 rpm at 4° C. for 10 minutes. The resulting precipitated DNA was then dried under reduced pressure. The thus recovered DNA powder was dissolved in 10 µl of water. Said DNA powder comprised the DNA fragment-β-2 which carried therein the desired, modified DNA-158N sequence.

EXAMPLE 3

The present Example illustrates the preparation of a DNA fragment carrying therein the DNA sequence which is designated as the modified DNA-166A sequence (namely, the DNA sequence having the nucleotide sequence of SEQ ID No. 7 of Sequence Listing) and is produced in accordance with the second aspect of the invention.

(1) Construction of Synthetic Oligonucleotide as Primer for PCR Method

A DNA synthesizer (Model-391; manufactured by Applied BioSystems, Co.) was used to produce by chemical synthesis a primer No. 4 which was the oligonucleotide having the nucleotide sequence shown in SEQ ID No. 10 of Sequence Listing.

(2) Preparation of Template for PCR Method

The vector pDAP8-1-XS, which is described above in the item (2) of Example 2, carries therein the DNA fragment which has a sequence length of about 1200 bp and which contains therein the DNA sequence of SEQ ID No. 1 of Sequence Listing (namely, the DHDPS-DNA-1143 sequence), and said DNA fragment has been inserted between the XbaI cleavage site and the SacI cleavage site in the vector pDAP8-1-XS.

This recombinant vector pDAP8-1-XS was used as the template in the present Example 3 to carry out the following PCR procedures.

(3) Amplification of the Required DNA Fragment by PCR, and Recovery thereof (i) First Step of PCR Method In order to produce the required DNA fragment by amplification according to the PCR method, the following reactions (A) and (B) were conducted as the first step of PCR method.

Thus, the reaction (A) comprised adding 5 µl of the recombinant plasmid vector pDAP8-1-XS for use as the template, as well as 1 µM of the primer FW-1, and 1 µM of the primer No. 4 of SEQ ID No. 10 to 100 µl of an amplification mixture [containing 10 mM Tris-HCl, pH 8.3, 1 mM MgCl$_2$, 50 mM KCl, a mixture of 0.2 mM each of 4 dNTPs, and 2.5 units of LA Taq DNA polymerase], followed by effecting the amplification reaction. The amplified DNA product so obtained is now referred to as DNA fragment-D.

Furthermore, the reaction (B) comprised adding 5 µl of the recombinant plasmid vector pDAP8-1-XS for use as the template, as well as 1 µM of the primer RV-1, and 1 µM of the BS KPN-1 to the amplification mixture of the same formulation as in the reaction (A), followed by effecting the amplification reaction. The amplified DNA product so produced by the reaction (B) is referred to as DNA fragment-B. The reaction (B) was conducted in a similar way as in the item (3) of Example 2.

The above amplification reaction was promoted by repeating 30 times a reaction cycle which consisted of three reaction procedures, namely denaturation at 94° C. for 30 seconds, annealing at 55° C. for 2 minutes, and extension at 72° C. for 2 minutes in a PCR reactor [Program Temp Control System PC-700; manufactured by Asthec, Co. Ltd.].

After the termination of the amplification reaction, the amplification reaction mixture coming from the reaction (A) was fractionated by low-melting agarose electrophoresis. And, a band containing the DNA fragment-D of 480 bp as the amplified DNA product was cut and separated out of the agarose gel. Furthermore, the amplification reaction mixture coming from the reaction (B) was fractionated by low-melting agarose electrophoresis. And, a band containing the DNA fragment-B of 1200 bp as the amplified DNA product was cut and separated out of the agarose gel.

From these gel bands so cut out and separated, a purified product of the DNA fragment-D and a purified product of the DNA fragment-B were separated respectively by means of Geneclean II Kit (manufactured by Funakoshi Co. Ltd.) and then recovered.

(ii) Second Step of PCR Method

The second step of the PCR method comprised adding 1 µl of the primer RV-1 and 1 µl of the primer FW-1, as well as 1 µl of the DNA fragment-D and 1 µl of the DNA fragment-B (which had been amplified individually by the reactions (A) and (B), respectively) to 100 µl of an amplification mixture [containing 10 mM Tris-HCl, pH 8.3, 1 mM MgCl$_2$, 50 mM KCl, a mixture of 0.2 mM each of 4 dNTPs, and 2.5 units of LA Taq DNA polymerase], followed by effecting the amplification reaction. This amplification was then effected by repeating 20 times a reaction cycle which consisted of three reaction procedures, namely denaturation at 94° C. for 30 seconds, annealing at 55° C. for 2 minutes, and extension at 72° C. for 2 minutes.

After the termination of the above amplification reaction the resultant amplification reaction solution was fractionated by low-melting agarose electrophoresis. Then, a band containing the desired DNA fragment-E of 1200 bp as the amplified DNA product was cut out of the agarose gel. From the gel band so cut out, a purified product of the DNA fragment-E was separated and recovered by means of Geneclean II Kit (manufactured by Funakoshi Co., Ltd.).

This DNA fragment-E is a DNA fragment of about 1350 bp, which carries therein the DNA-166A sequence (a length of 1143 bp) having the nucleotide sequence of SEQ ID No. 7 of Sequence Listing, and which has a KpnI cleavage site at upstream of the 5' terminus of the DNA-166A sequence and has an SacI cleavage site at downstream of the 3' terminus of the DNA-166A sequence.

(4) Cloning of the DNA Fragment Carrying the Modified DNA-166A Sequence

The DNA fragment-E produced as above was used to produce the DNA fragment carrying the desired, modified DNA-166A sequence by cloning. A sufficient amount of said DNA fragment to be produced was obtained according to the following procedures.

(i) 10 µl of the DNA fragment-E produced as above was first digested with 10 units each of restriction endonucleases KpnI and SacI in an L buffer (manufactured by TaKaRa Brewery Co., Ltd.). The DNA fragment as produced by this digestion is now referred to as DNA fragments. Further, 10 µl of the pBluescript II SK(+) was digested with 10 units each of KpnI and SacI in an L buffer (manufactured by TaKaRa Brewery Co., Ltd.), to prepare a truncated plasmid. The resulting digested mixture containing the DNA fragment-γ, as well as the resulting digested mixture containing the truncated plasmid were added individually with a 1/10-fold volume of 3 M sodium acetate and a 2-fold volume of ethanol. The resulting mixtures were each incubated at −20° C. for about 6 hours. Thereafter, the resulting individual incubated mixtures were each centrifuged, to produce the precipitated DNA, which was separated, dried and dissolved in 5 µl of water.

Thus, there were prepared the aqueous solution of the DNA fragment-γ, as well as the aqueous solution of the truncated DNA. These two aqueous solutions were mixed together at each volume of 5 μl. The resulting mixture (10 μl) was subjected to a ligation reaction with using a DNA ligation kit (manufactured by TaKaRa Brewery Co., Ltd.), so that the two DNAs contained in said resulting mixture were ligated with each other. To the resulting ligation reaction mixture were added a 1/10-fold volume of 3 M sodium acetate and a 2-fold volume of ethanol. The resulting admixture was incubated at −20° C. for about 6 hours. The resulting incubated admixture was centrifuged to precipitate the ligated DNA, which was then separated and dried. The thus recovered DNA was further dissolved in 5 μl of water to prepare an aqueous solution of said DNA.

The DNA which is contained in the resultant aqueous solution was a double-stranded recombinant plasmid (that is, the pBluescript-DNA-166A plasmid described hereinbefore) which was prepared by ligating said DNA fragment-γ with said truncated plasmid as produced by the cleavage of the plasmid vector pBluescript II SK(+) with KpnI and SacI, and in which the modified DNA-166A sequence was carried within the inserted DNA region of the recombinant plasmid.

(ii) *Escherichia coli* XL1-Blue MRF' was then transformed by integrating the above-mentioned pBluescript-DNA-166A plasmid therein. Further, the so transformed *Escherichia coli* cells were cultured in a liquid culture medium.

From the culture of the so transformed *Escherichia coli* cells was then extracted the recombinant plasmid. In this manner, the recombinant plasmid carrying therein the modified DNA-166A sequence could be cloned.

(5) Recovery of the DNA Fragment Carrying therein the Modified DNA-166A Sequence 10 μl of the plasmid DNA of the so produced pBluescript-DNA-166A plasmid was then digested with 10 units of XbaI and 10 units of SacI in a buffer M (manufactured by TaKaRa Brewery Co., Ltd.). The resulting digested mixture was fractionated by low-melting agarose electrophoresis. The gel band which contained therein the so produced DNA fragment-γ-2 carrying the DNA-166A sequence (of a length of 1143 bp) was cut out of the agarose gel. The so cut-out agarose gel band containing the DNA fragment-γ-2 therein was added with an equal volume of a TE buffer (containing 10 mM Tris-HCl, pH 8 and 1 mM EDTA). The resulting mixture was heated at 68° C. for 20 minutes, to dissolve the agarose. The resulting solution of the agarose was extracted twice with aqueous saturated phenol, to remove the agarose. The resulting phenol extract containing the DNA therein were added with a 1/10-fold volume of 3 M sodium acetate and a 2-fold volume of ethanol. The resulting mixture was incubated at −20° C. for about 6 hours. The resulting incubated mixture was centrifuged at 15,000 rpm at 4° C. for 10 minutes. The resulting precipitated DNA was then separated and dried under reduced pressure. The so recovered powder of the DNA was dissolved in 10 μl of water. This DNA powder was formed of the DNA fragment-γ-2 of about 1200 bp carrying therein the desired, modified DNA-166A sequence.

Further, in the same manner as described in Example 1, item (7) hereinbefore, the DNA fragment-β-2 which was produced in Example 2, item (5) herinbefore was examined by an automatic DNA sequencer, namely ALF DNA Sequencer II, with using of a nucleotide sequencing kit. It was thus convinced that the said DNA fragment-β-2 was a DNA fragment which carried therein the modified DNA-158N sequence having the nucleotide sequence of SEQ ID No. 5 of Sequence Listing.

Equally, the said DNA fragment-γ-2 as produced in Example 3, item (5) above was examined by the nucleotide-sequencing experiments in the same manner as described just above. The said DNA fragment-γ-2 was verified to be a DNA fragment which carried therein the modified DNA-166A sequence having the nucleotide sequence of SEQ ID No. 7 of Sequence Listing.

EXAMPLE 4

The present Example illustrates a method for transforming a rice plant, which comprises introducing the DNA sequence of the first aspect of the invention or the modified DNA sequence of the second aspect of the invention, as an exogenous gene, into the rice plant.

(1) Construction of Recombinant Vector for use in the Introduction of Exogenous Gene (i) The DNA (10 μl) of plasmid vector pBI221, which was of 5.7-kb-length and carried therein the 35S promoter of cauliflower mosaic virus, the NOS terminator and the ampicillin-resistant gene (manufactured by Clontech, Co.), was digested with restriction endonucleases XbaI and SacI in a buffer M (manufactured by TaKaRa Brewery Co., Ltd.). From the resulting digestion mixture was precipitated the DNA, which was collected by centrifugation and then dried. A vector fragment of about 3.8 kb, which carried the 35S promoter and NOS terminator therein, was thus harvested.

(ii) The vector fragment so obtained was dissolved in 5 μl of water. The resulting aqueous solution (5 μl) of said vector fragment was mixed with an aqueous solution (5 μl) of the aforesaid DNA fragment-XS which was a DNA of about 1143 bp carrying therein the DHDPS-DNA-1143 sequence (of 1143 bp) described in SEQ ID No. 1, and which was produced in Example 2 hereinbefore according to the first aspect of the invention.

The resulting mixture was treated with a DNA ligation kit (manufactured by TaKaRa Brewery Co., Ltd.), to effect ligation of the DNAS. In this manner, there was prepared a cyclic recombinant vector which was formed by ligating said DNA fragment-XS with the XbaI/SacI-cleaved vector fragment derived from the plasmid vector pBI221. The cyclic recombinant vector so prepared is hereinafter referred to as vector pDAP. This vector pDAP was of a 4.9-kb length and had such a structure where the DNA fragment-XS region thereof was inserted and ligated between the 35S promoter region and the NOS terminator region of the vector pDAP and the ampicillin-resistant gene (Am$^r$) was incorporated in the recombinant vector.

(iii) The DNA fragment-β-2 as produced in Example 2 (that is, the DNA of a size of about 1143 bp, which carried therein the modified DNA-158N sequence of 1143 bp described in SEQ ID No. 5 as provided in the second aspect of the invention) was employed instead of the DNA fragment-XS produced above in Example 2, to carry out the ligation reaction similarly to Example 4, (ii) above. Thereby, the DNA fragment-β-2 was ligated to the XbaI/SacI-cleaved vector fragment of the plasmid vector pBI221 to prepare a cyclic recombinant vector, which is hereinafter is referred to as vector p158N. This recombinant vector 158N was of a 4.9-kb length and had such a structure that the DNA fragment-β-2 region thereof was inserted and ligated between the 35S promoter region and the NOS terminator region of the recombinant vector.

(iv) Further, the DNA fragment-γ-2 as produced in Example 3 (that is, the DNA of a size of about 1143 bp, which carried therein the modified DNA-166A sequence of 1143 bp of described as SEQ ID No. 7 as provided in the second aspect of the invention) was employed instead of the DNA fragment-XS produced in Example 2, to carry out the ligation reaction similarly. Thereby, the DNA fragment-γ-2 was ligated to the XbaI/SacI-cleaved vector fragment of the plasmid vector pBI221, to prepare a cyclic recombinant vector, which is now referred to as vector p166A. This recombinant vector 166A was of a 4.9-kb length and had such a structure that the DNA fragment-γ-2 region thereof was inserted and ligated between the 35S promoter region and the NOS terminator region of the recombinant vector.

(2) Cloning of the Recombinant Vector

The aqueous solution (10 μl) of either the recombinant vector pDAP or the recombinant vector p158N or the recombinant vector p166A obtained as above (containing 10 mg of the DNA in the solution) and 100 μl of a commercially available *Escherichia coli* XL1-Blue MRF' competent cells were placed together in a 1.5-ml tube. The resulting mixture in the tube was incubated on ice bath for 30 minutes, then at 42° C. for 30 seconds, and again on ice bath for 2 minutes. After this incubation, the incubated mixture was treated in the same manner as described in the item (6) of Example 1 hereinbefore, followed by culturing the transformed *Escherichia coli* cells under shaking.

The resulting culture of the transformed cells of *Escherichia coli* was plated on an LB agar medium as supplemented with ampicillin and the other additives, in the same manner as described in the item (6) of Example 1. The bacteria cells were cultured on the medium at 37° C. for 16 hours.

In this way, there were obtained 10 colonies of the transformed *Escherichia coli* cell which was resistant to ampicillin and had been transformed by the integration therein of the recombinant vector pDAP or the recombinant vector 158N or the recombinant vector 166A. These ten colonies of the transformed *Escherichia coli* cell were proliferated in a liquid culture medium containing 50 mg/l of ampicillin.

(3) Recovery of the Recombinant Vector

From the so proliferated cells of the transformed *Escherichia coli* bacteria present in each of the said 10 colonies, there were isolated and purified the recombinant plasmids by means of a plasmid purification kit (QIA Filter Plasmid Midi Kit; manufactured by QIAGEN, CO. LTD.).

The ten lots of the recombinant plasmids so obtained were digested with restriction endonucleases XbaI and SacI, respectively. Then, the resulting digested DNA fragments were individually analyzed by agarose gel electrophoresis.

With making reference to the results of the above analysis, such a recombinant plasmid, which carried therein the DHDPS-DNA-1143 sequence of the first aspect of the invention as normally inserted at downstream of the 35S promoter region of the recombinant vector, was selected from among the recombinant plasmids as isolated in the above and then was harvested as the vector pDAP.

In the same manner as above, further such a recombinant plasmid which carried therein the modified DNA-158N sequence of the second aspect of the invention as normally inserted at downstream of the 35S promoter region, was selected from among the recombinant plasmids as isolated in the above, and then was harvested as the vector p158N.

In the same manner as above, still additionally, such a recombinant plasmid, which carried therein the modified DNA-166N sequence of the second aspect of the invention as normally inserted at downstream of the 35S promoter region, was selected from among the isolated recombinant vectors and then was harvested as the vector p166A.

The *Escherichia coli* XL1-Blue MRF' strain, which has been transformed by the integration therein of the recombinant vector p158N as above, is designated as *Escherichia coli* XL1-Blue MRF'/p158N, and has been deposited under Accession No. FERM BP-6323 in terms of the Budapest Treaty since Apr. 13, 1998 at the National Institute of Bioscience and Human-Technology, the Agency of Industrial Science and Technology, supra., in Japan.

The *Escherichia coli* XL1-Blue MRF' strain, which has been transformed by the integration therein of the recombinant vector p166A as above, is designated as *Escherichia coli* XL1-Blue MRF'/p166A, and has been deposited under Accession No. FERM BP-6324 in terms of the Budapest Treaty since Apr. 13, 1998 at the same National Institute, supra., in Japan.

(4) Preparation of Rice Callus

The ripe seeds of completely fructifying rice (variety: Nipponbare) were hulled. The resulting hulled rice seeds with outer skin were sterilized by sequential immersions thereof in an aqueous 70% ethanol solution for 60 seconds and then in a dilute aqueous solution containing sodium hypochlorite at an effective chlorine content of about 1%, for 6 minutes. The sterilized rice seeds were rinsed in sterile water.

In an MS medium containing the usual inorganic components and further supplemented with 30 g/liter of sucrose, a plant hormone of 2,4-PA of 2 mg/liter and 8 g/liter of agar, there were placed the above, sterilized rice seeds. The rice seeds were then incubated at 28° C. under irradiation of light at 2000 lux for 16 hours per day for 45 days. The callus was thus formed from the seed. The calluses were cut off out of the albumen part of the incubated seeds, followed by sieving with a stainless-mesh sieve of a pore size of 1 mm. There were obtained calluses each of a dimension of 1 mm or less at a cell amount of 3 ml in term of PCV (packed cell volume: the quantity of compressed cells).

(5) Preparation of Whiskers

Commercially available whiskers (LS20; manufactured by Titanium Industry, Co., Ltd.) made of potassium titanate were placed in a tubular container of 1.5 ml capacity and then sterilized overnight in 0.5 ml of ethanol as add in the small tubular container. The ethanol was removed completely by evaporation, and the sterilized whiskers were recovered. Sterile water was placed in the tubular container containing the sterilized whiskers therein, and the contents in the tube; were agitated. The whiskers and the sterile water together were centrifuged, and the supernatant water was discarded. The whiskers were thus rinsed. The whiskers-rinsing procedure was repeated three times. Thereafter, 0.5 ml of the R2 liquid medium was added to the tubular container, to prepare a suspension of the whiskers in the medium.

(6) Preparation of Materials to be Used for Introduction of Exogenous Gene into Rice Callus Cell The recombinant vector pDAP, or the recombinant vector p158N, or the recombinant vector p166A, which were prepared as described above in the item (3) of Example 4, was dissolved at a concentration of 1 mg/ml in a TE buffer (comprising 10 mM Tris-HCl, 1 mM EDTA, pH 8), to prepare a solution of the recombinant vector.

In the tubular container containing therein the suspension of the whiskers, there were charged 250 μl of the calluses each of a dimension of 1 mm or less. The resulting mixture in the container was then agitated together and subsequently centrifuged at 1,000 rpm for 10 seconds, to precipitate the calluses and whiskers. The resulting supernatant was discarded, and a mixture of the rice callus cells and the whiskers was afforded.

To the mixture of the callus cells and the whiskers present in the tube, there were added 10 μl (with a DNA content of 10 μl) of the said recombinant vector (namely, the vector PDAP or the vector p158N or the vector p166A) and 10 μl (with a DNA content of 10 μl) of a plasmid vector p35SC-SS which carried therein a gene resistant to a herbicide, phosphinothricin, as the selection marker (see JP-A-8-154513). After sufficient shaking, the resultant homogenous mixture was recovered.

The tube containing therein said homogenous mixture was centrifuged at 18,000×g for 5 minutes. After this centrifugation, the mixture contained in the tube was again shaken together. This centrifugation procedure and re-shaking procedure were individually repeated three times.

(7) Manipulation for Introduction of the Exogenous Gene into Rice Callus

The tube, which was containing therein the resultant homogenous mixture comprising the callus cells, the whiskers, and the recombinant vector carrying therein the DNA of this invention and also the plasmid vector p35SC-SS, prepared as above, was placed in the bath vessel of an ultrasonic generator, so that the whole tube was sinked within the bath. The ultrasonic wave at a frequency of 40 kHz was irradiated onto the tube at an intensity of 0.25 W/cm$^2$ for one minute. After this irradiation, the so ultrasonically treated mixture was incubated at 4° C. for 30 minutes.

The mixture thus treated ultrasonically was then rinsed with the R2 liquid medium, and there were afforded the desired, transformed callus cells which carried said recombinant vector as introduced therein.

(8) Selection of the Callus Cells as Transformed by the Introduced Vector

The resultant calluses having the transformed cells in which the recombinant vector was introduced as above, were placed in a 3.5-cm petri dish, to which was then added a volume of the R2 liquid medium containing the usual inorganic components and further supplemented with 30 g/liter of sucrose and 2 mg/liter of 2,4-PA. Subsequently, the transformed callus cells were cultivated at 28° C. under shaking on a rotary shaker (at 50 rpm.) and under irradiation of light at 2,000 lux for 16 hours per day, to produce the divided callus cells through the cell-division.

On the 3$^{rd}$ day of cultivation, the resultant suspension (3 ml) of the divided cells was spread evenly on a medium which had been prepared by admixing the N6 medium containing the usual inorganic components, with 30 g/liter of sucrose, 2 mg/liter of 2,4-PA, 3 g/liter of Gelrite and 30 mg/liter of phosphinothricin. Then, the cells on the medium were cultured at 28° C. under irradiation of light at 2000 lux for 16 hours per day, for consecutive 30 days. The phosphinothricin-resistant transformed callus cells were produced and obtained thereby.

(9) Re-selection of the Transgenic Callus Cell as Taransformed by the Vector p158N or p166A From among the phosphinothricin-resistant transgenic cultured callus cells so obtained, there was re-selected only such a desired cultured cells which had been transformed by the introduction of a sufficient amount of the DNA of the second aspect of this invention as the exogenous gene. For this purpose, 400 calluses composed of said transformed callus cells (each having a 2-mm diameter) were transplanted onto a culture medium which was prepared by admixing the N6 medium of the inorganic component composition with 30 g/liter of sucrose, 2 mg/liter of 2,4-PA, 3 g/liter of Gelrite and 200 mg/liter of a lysine-analog, S-(2-aminoethyl)cysteine (referred to as "AEC" hereinafter) usable as a cell-proliferation-inhibitor. The calluses composed of the transformed callus cells so transplanted were cultured at 28° C. under irradiation of light at 2,000 lux for 16 hours per day, for consecutive 30 days. The calluses composed of the transformed callus cells carrying therein the vector p158N or p166A, which could grow in the culture medium containing the added AEC, were re-selected in the above manner.

(10) Regeneration of Plant from the Transformed Callus Cells so Re-selected 98 to 100 calluses (each of a 5-mm diameter) comprising the phosphinothricin-resistant and AEC-resistant transformed callus cells as obtained in the above were transplanted onto a culture medium which was prepared by admixing the MS medium of the inorganic component composition with 30 g/liter of sucrose, 2 mg/liter of benzyladenine, 1 mg/liter of naphthalene acetate, and 3 g/liter of Gelrite. The calluses composed of the trans-formed callus cells so transplanted were then cultured at 28° C. under irradiation of light at 2,000 lux for 16 hours per day, for consecutive 30 days. From the calluses composed of the transformed callus cells so cultured were regenerated the bud and root of the rice plant. The plumules having the regenerated buds and roots were grown to a height of 10 to 30 mm, and the grown plumules were transplanted into an MS medium which was further supplemented with 30 g/liter of sucrose and 3 g/liter of Gelrite and which was placed in a test tube of a diameter of 45 mm and a length of 25 cm. The transplanted plumules were cultivated therein for 20 days, to afford the transgenic rice plants.

By conducting the aforementioned method, 80 plants of the transgenic rice plant could be regenerated from 98 calluses composed of the transformed callus cells which carried therein the DHDPS-DNA-1143 sequence of the first aspect of the invention as the exogenous gene. Further, 76 plants of the transgenic rice plant could be regenerated from 100 calluses composed of the AEC-resistant transformed callus cells which carried therein the modified DNA-158N sequence of the second aspect of the invention as the exogenous gene.

Furthermore, 79 plants of the transgenic rice plant could be regenerated from 100 calluses composed of the AEC-resistant transformed callus cells which carried therein the modified DNA-166N sequence of the second aspect of the invention as the exogenous gene.

(11) Genetic Analysis of the Regenerated Plant Body of the Transgenic Rice Plant The DNA for encoding the DHDPS present in the so regenerated transgenic rice plant was analyzed by PCR method according to the following procedure.

(i) From the regenerated transgenic rice plant as produced in the above item (10) were collected the leaves. 50 mg of such leaves was placed in a 1.5-ml capacity microtube, to which was then added 300 μl of 20 mM Tris-HCl buffer (pH 7.5) containing 10 mM EDTA. The leaves in the buffer were disrupted. To the disrupted leaves was added 20 μl of 20% SDS, followed by heating at 65° C. for 10 minutes. The resulting mixture was added with 100 μl of 5M potassium acetate and the resulting admixture was left to stand on ice bath for 20 minutes and then centrifuged at a centrifugal acceleration rate of 17,000×g for 20 minutes. 200 μl of isopropanol was added to the resulting supernatant. The resulting mixture in the tube was agitated by tumbling of the tube. The agitated mixture was then centrifuged at centifugal acceleration rate of 17,000×g for 20 minutes. The resulting precipitated DNA was separated and dried under reduced pressure. The DNA so obtained was dissolved in 100 μl of a TE buffer.

(ii) Further, an oligonucleotide of the nucleotide sequence of SEQ ID No. 14 of Sequence Listing and an oligonucleotide of the nucleotide sequence of SEQ ID No. 15 of Sequence Listing were prepared as primers for PCR.

5 μl of the above-mentioned DNA derived from the regenerated transgenic rice plant was used as template, and 1 μM each of the above-mentioned two types of the oligonucleotides were used as primers. They were then added to 100 μl of an amplification mixture [containing 10 mM Tris-HCl, pH 8.3, 1.0 mM $MgCl_2$, 50 mM KCl, 0.01% gelatin, pH 8.3, a mixture of 4 dNTPs each at 0.2 mM, and a Taq DNA polymerase of 2.5 units], followed by effecting the amplification reaction of DNA. The amplification mixture herein used had been prepared by using a PCR kit (PCR Amplification Kit; manufactured by TaKaRa Brewery, Co., Ltd.).

The amplification reaction was effected by repeating 30 times a reaction cycle which consisted of three reaction procedures, namely denaturation at 94° C. for one minute, annealing at 60° C. for 30 seconds and extension at 72° C. for one minute.

(iii) The resulting PCR reaction solution was then subjected to agarose electrophoresis in a conventional manner. Thereby, detection could be made of various fragments of DNAs which had been amplified from the DNAs as extracted from the regenerated transgenic rice plant.

Further analysis of the sequences of the resultant various DNA fragments was conducted by means of a nucleotide sequencing kit, to verify that a DNA fragment, which was corresponding to the DHDPS-DNA-1143 sequence or the modified DNA-158N or the modified DNA-166A sequence of this invention, was present in the said resultant various DNA fragments which were extracted from the regenerated transgenic rice plant in the above manner.

By conducting the genetic analysis as above by PCR, it could be confirmed that there were produced the regenerated transgenic rice plants which necessarily carried therein the introduced exogenous gene. The regenerated rice plants so confirmed were then transplanted and cultivated in pot containing therein cultivation soil. These regenerated rice plants so transplanted could normally grow further so that their self-fertilized seeds could be yielded and recovered.

(12) Assay of Lysine Content of the Regenerated Plant Body of Transgenic Rice Plant Green leaves were harvested respectively from the regenerated transgenic rice plant having the plant cells which carried the introduced recombinant vector pDAP containing therein the DHDPS-DNA-1143 sequence of the first aspect of the invention, and also from the regenerated transformant rice plant having the plant cells which carried the introduced recombinant vector pDNA-158N containing therein the DNA-158N sequence of the second aspect of the invention, as well as from the regenerated transgenic rice plant having the plant cells which carried the introduced recombinant vector pDNA-166A containing therein the DNA-166A sequence of the second aspect of the invention.

One gram each of the green leaves harvested individually from the transgenic rice plants was placed in a first tube of a 1.5-ml capacity, to which was added then 1 ml of 50% acetonitrile, followed by disrupting these leaves. The disputed leave mixture so obtained was transferred to a second tube of a 1.5 ml capacity, and was centrifuged at a centrifugal acceleration rate of 17,000×g for 20 minutes. The resulting supernatant was transferred in a third tube, to which was then added 1 ml of 50% acetonitrile. The mixture in the third tube was agitated by inverting the tube upside down, followed by re-centrifugation of the mixture. The resulting supernatant was added to the first tube. These procedures were repeated three times. In this manner, there was prepared a solution in acetonitrile of lysine which was extracted and recovered from the green leaves.

The acetonitrile solution of lysine so extracted was absolutely evaporated to dryness under reduced pressure. The solid residue was added with 1 ml of distilled water, to prepare an aqueous solution thereof. Each of the aqueous solutions so prepared was centrifuged at 17,000×g for 20 minutes, to afford the supernatant of 0.5 ml. With 100 μl of each supernatant so obtained was mixed 100 μl of 5 mM DNFB (2,4-dinitro-1-fluorobenzene). The resulting mixture was incubated overnight. To each of the resulting incubation mixtures was added 200 μl of acetonitrile, followed by agitation and centrifugation at 17,000×g for 20 minutes. Thereby, an extract solution of lysine was recovered as these resulting supernatant solutions. The resulting extract solutions were individually subjected to high-performance liquid chromatography (HPLC) device (Type 8020; manufactured by Tosoh, Co., Ltd.), to determine the free lysine content in each extract. The column used in this HPLC was CAPCELL PAK-C18 (manufactured by Shiseido, Co., Ltd.). The HPLC was conducted with using acetonitrile/water as the development solvent with a concentration gradient of acetonitrile of from 60% to 72% and at the flow of 0.8 ml/min. The lysine content was determined by measurement of the absorbance of light at 350 nm.

As a control rice plant was used a plant of an ordinary rice plant (variety: Nipponbare). The results of the determination as obtained are shown in Table 1 below.

TABLE 1

| rice plant tested | Content of free lysine (n mol/FW g) |
|---|---|
| Control rice plant | 59 |
| rice plant carrying vector pDAP | 360 |
| rice plant-1 carrying vector p158N | 688 |
| rice plant-2 carrying vector p158N | 652 |
| rice plant-1 carrying vector p166A | 673 |

As will be clear from the results shown in Table 1, it is confirmed that the content of the free lysine produciable in the rice plant can be elevated by introducing the novel DNA sequences as an exogenous gene into the rice plant, with using a recombinant vectors which carries a promoter capable of expressing in the plant cell.

Industrial Utilizability

As will be obvious from the foregoing descriptions, this invention provides such novel DNA sequences for encoding the dihydrodipicolinate synthase of rice. By introducing the DNA sequences of this invention as the exogenous gene in a rice plant, it is made feasible to increase the content of lysine which is one of the essential amino acids in the rice plant. The DNA sequences provided in accordance with this invention can be introduced as an exogenous gene into the rice plant and into other useful plants such as corn, soybean, wheat and barley by a conventional and known biotechnological method. Thus, the DNA sequences provided in accordance with this invention are useful for cultivation of novel varieties of plant which are capable of generating seeds of high lysine content.

What is claimed is:

1. An isolated DNA molecule for encoding the rice dihydrodipicolinate synthase which has the amino acid sequence shown in SEQ ID No. 2 of Sequence Listing.

2. An isolated DNA molecule for encoding a protein having the amino acid sequence shown in SEQ ID No. 6 of the Sequence Listing and having dihydrodipicolinate synthase activity.

3. An isolated DNA molecule for encoding a protein having the amino acid sequence shown in SEQ ID No. 8 of the Sequence Listing and having dihydrodipicolinate synthase activity.

* * * * *

SEQUENCE LISTING

<160> NUMBER OF SEQ ID NOS: 15

<210> SEQ ID NO 1
<211> LENGTH: 1143
<212> TYPE: DNA
<213> ORGANISM: Oryza sativa
<220> FEATURE:
<221> NAME/KEY: CDS
<222> LOCATION: (1)..(1143)

<400> SEQUENCE: 1

| | | | | | | | | | | | | | | | | |
|---|---|---|---|---|---|---|---|---|---|---|---|---|---|---|---|---|
| atg | gcg | tcg | ctg | ctg | atc | gcc | agc | acg | ggg | ggc | tgc | cca | ccg | cct | cgc | 48 |
| Met | Ala | Ser | Leu | Leu | Ile | Ala | Ser | Thr | Gly | Gly | Cys | Pro | Pro | Pro | Arg | |
| 1 | | | | 5 | | | | | 10 | | | | | 15 | | |
| gtg | gaa | gga | cgc | cgc | cgc | cct | ggg | acc | cgc | tcc | ggc | ttg | gcg | cga | cct | 96 |
| Val | Glu | Gly | Arg | Arg | Arg | Pro | Gly | Thr | Arg | Ser | Gly | Leu | Ala | Arg | Pro | |
| | | | 20 | | | | | 25 | | | | | 30 | | | |
| tgg | ccc | gcc | gcc | gtg | gct | gca | ccg | gcg | ccg | ctc | ctc | agg | att | agc | aga | 144 |
| Trp | Pro | Ala | Ala | Val | Ala | Ala | Pro | Ala | Pro | Leu | Leu | Arg | Ile | Ser | Arg | |
| | | 35 | | | | | 40 | | | | | 45 | | | | |
| gga | aag | ttt | gca | ttg | cag | gcc | atc | acc | ctt | gat | gat | tat | ctt | cca | atg | 192 |
| Gly | Lys | Phe | Ala | Leu | Gln | Ala | Ile | Thr | Leu | Asp | Asp | Tyr | Leu | Pro | Met | |
| | 50 | | | | | 55 | | | | | 60 | | | | | |
| cga | agt | act | gaa | gtg | aaa | aat | cgg | aca | tca | aca | gct | gat | atc | act | agt | 240 |
| Arg | Ser | Thr | Glu | Val | Lys | Asn | Arg | Thr | Ser | Thr | Ala | Asp | Ile | Thr | Ser | |
| 65 | | | | | 70 | | | | | 75 | | | | | 80 | |
| ctc | aga | gta | att | aca | gcg | gtc | aaa | acc | cca | tat | ctg | cct | gat | gga | aga | 288 |
| Leu | Arg | Val | Ile | Thr | Ala | Val | Lys | Thr | Pro | Tyr | Leu | Pro | Asp | Gly | Arg | |
| | | | | 85 | | | | | 90 | | | | | 95 | | |
| ttt | gat | ctc | gaa | gca | tat | gat | tca | ctg | ata | aat | atg | cag | ata | gat | ggt | 336 |
| Phe | Asp | Leu | Glu | Ala | Tyr | Asp | Ser | Leu | Ile | Asn | Met | Gln | Ile | Asp | Gly | |
| | | | 100 | | | | | 105 | | | | | 110 | | | |
| ggt | gct | gaa | ggt | gta | ata | gtt | gga | gga | aca | aca | gga | gag | ggc | cac | ctt | 384 |
| Gly | Ala | Glu | Gly | Val | Ile | Val | Gly | Gly | Thr | Thr | Gly | Glu | Gly | His | Leu | |
| | | 115 | | | | | 120 | | | | | 125 | | | | |
| atg | agc | tgg | gat | gaa | cac | atc | atg | ctt | att | gga | cat | act | gtt | aac | tgc | 432 |
| Met | Ser | Trp | Asp | Glu | His | Ile | Met | Leu | Ile | Gly | His | Thr | Val | Asn | Cys | |
| | 130 | | | | | 135 | | | | | 140 | | | | | |
| ttt | ggt | gct | aaa | gtt | aaa | gtg | gta | ggc | aac | aca | ggt | agt | aac | tca | aca | 480 |
| Phe | Gly | Ala | Lys | Val | Lys | Val | Val | Gly | Asn | Thr | Gly | Ser | Asn | Ser | Thr | |
| 145 | | | | | 150 | | | | | 155 | | | | | 160 | |
| aga | gag | gct | att | cat | gca | aca | gag | cag | gga | ttt | gct | gta | ggt | atg | cat | 528 |
| Arg | Glu | Ala | Ile | His | Ala | Thr | Glu | Gln | Gly | Phe | Ala | Val | Gly | Met | His | |
| | | | | 165 | | | | | 170 | | | | | 175 | | |
| gcg | gct | ctc | cat | atc | aat | cct | tac | tat | ggg | aag | acc | tct | atc | gaa | ggg | 576 |
| Ala | Ala | Leu | His | Ile | Asn | Pro | Tyr | Tyr | Gly | Lys | Thr | Ser | Ile | Glu | Gly | |
| | | | 180 | | | | | 185 | | | | | 190 | | | |
| ttg | ata | tct | cat | ttt | gag | gct | gtc | ctc | cca | atg | ggt | cca | acc | att | att | 624 |
| Leu | Ile | Ser | His | Phe | Glu | Ala | Val | Leu | Pro | Met | Gly | Pro | Thr | Ile | Ile | |
| | | 195 | | | | | 200 | | | | | 205 | | | | |
| tac | aat | gtt | cca | tct | agg | act | ggc | cag | gat | att | cct | cct | gca | gtt | att | 672 |
| Tyr | Asn | Val | Pro | Ser | Arg | Thr | Gly | Gln | Asp | Ile | Pro | Pro | Ala | Val | Ile | |
| | 210 | | | | | 215 | | | | | 220 | | | | | |
| gag | gct | gtt | tca | agt | ttc | aca | aac | ttg | gca | ggt | gtg | aaa | gaa | tgt | gtt | 720 |
| Glu | Ala | Val | Ser | Ser | Phe | Thr | Asn | Leu | Ala | Gly | Val | Lys | Glu | Cys | Val | |
| 225 | | | | | 230 | | | | | 235 | | | | | 240 | |
| gga | cat | gag | agg | gtt | aag | tgc | tac | act | gac | aaa | ggt | ata | acc | ata | tgg | 768 |
| Gly | His | Glu | Arg | Val | Lys | Cys | Tyr | Thr | Asp | Lys | Gly | Ile | Thr | Ile | Trp | |
| | | | | 245 | | | | | 250 | | | | | 255 | | |

```
agt ggt aat gat gat gaa tgc cat gat tct agg tgg aaa tat ggt gcc    816
Ser Gly Asn Asp Asp Glu Cys His Asp Ser Arg Trp Lys Tyr Gly Ala
        260                 265                 270 act gga gtt att tct gtg gct agc aac ctt att cct ggt ctc atg cac    864
Thr Gly Val Ile Ser Val Ala Ser Asn Leu Ile Pro Gly Leu Met His
    275                 280                 285 gat ctc atg tat gaa ggg gag aat aag acg cta aat gag aag ctc ttt    912
Asp Leu Met Tyr Glu Gly Glu Asn Lys Thr Leu Asn Glu Lys Leu Phe
290                 295                 300 ccc ctg atg aaa tgg ttg ttt tgc cag cca aat cca att gct ctc aac    960
Pro Leu Met Lys Trp Leu Phe Cys Gln Pro Asn Pro Ile Ala Leu Asn
305                 310                 315                 320 act gcc ctg gct cag ctt gga gtg gta agg cct gtt ttc aga tta cca   1008
Thr Ala Leu Ala Gln Leu Gly Val Val Arg Pro Val Phe Arg Leu Pro
        325                 330                 335 tat gta cct ctt cct ctt gaa aag agg gta gag ttt gtc cga atc gtt   1056
Tyr Val Pro Leu Pro Leu Glu Lys Arg Val Glu Phe Val Arg Ile Val
        340                 345                 350 gaa tct att gga cgg gaa aac ttt gtg ggt gag aac gag gca cgg gtt   1104
Glu Ser Ile Gly Arg Glu Asn Phe Val Gly Glu Asn Glu Ala Arg Val
    355                 360                 365 ctt gac gac gat gat ttt gtg ttg gtc agt agg tac taa               1143
Leu Asp Asp Asp Asp Phe Val Leu Val Ser Arg Tyr
    370                 375                 380

<210> SEQ ID NO 2
<211> LENGTH: 380
<212> TYPE: PRT
<213> ORGANISM: Oryza sativa

<400> SEQUENCE: 2

Met Ala Ser Leu Leu Ile Ala Ser Thr Gly Gly Cys Pro Pro Pro Arg
1               5                   10                  15

Val Glu Gly Arg Arg Pro Gly Thr Arg Ser Gly Leu Ala Arg Pro
            20                  25                  30

Trp Pro Ala Ala Val Ala Ala Pro Ala Pro Leu Leu Arg Ile Ser Arg
        35                  40                  45

Gly Lys Phe Ala Leu Gln Ala Ile Thr Leu Asp Asp Tyr Leu Pro Met
    50                  55                  60

Arg Ser Thr Glu Val Lys Asn Arg Thr Ser Thr Ala Asp Ile Thr Ser
65                  70                  75                  80

Leu Arg Val Ile Thr Ala Val Lys Thr Pro Tyr Leu Pro Asp Gly Arg
                85                  90                  95

Phe Asp Leu Glu Ala Tyr Asp Ser Leu Ile Asn Met Gln Ile Asp Gly
            100                 105                 110

Gly Ala Glu Gly Val Ile Val Gly Gly Thr Thr Gly Glu Gly His Leu
        115                 120                 125

Met Ser Trp Asp Glu His Ile Met Leu Ile Gly His Thr Val Asn Cys
    130                 135                 140

Phe Gly Ala Lys Val Lys Val Val Gly Asn Thr Gly Ser Asn Ser Thr
145                 150                 155                 160

Arg Glu Ala Ile His Ala Thr Glu Gln Gly Phe Ala Val Gly Met His
                165                 170                 175

Ala Ala Leu His Ile Asn Pro Tyr Tyr Gly Lys Thr Ser Ile Glu Gly
            180                 185                 190

Leu Ile Ser His Phe Glu Ala Val Leu Pro Met Gly Pro Thr Ile Ile
        195                 200                 205
```

-continued

```
Tyr Asn Val Pro Ser Arg Thr Gly Gln Asp Ile Pro Pro Ala Val Ile
    210                 215                 220

Glu Ala Val Ser Ser Phe Thr Asn Leu Ala Gly Val Lys Glu Cys Val
225                 230                 235                 240

Gly His Glu Arg Val Lys Cys Tyr Thr Asp Lys Gly Ile Thr Ile Trp
                245                 250                 255

Ser Gly Asn Asp Asp Glu Cys His Asp Ser Arg Trp Lys Tyr Gly Ala
                260                 265                 270

Thr Gly Val Ile Ser Val Ala Ser Asn Leu Ile Pro Gly Leu Met His
            275                 280                 285

Asp Leu Met Tyr Glu Gly Glu Asn Lys Thr Leu Asn Glu Lys Leu Phe
290                 295                 300

Pro Leu Met Lys Trp Leu Phe Cys Gln Pro Asn Pro Ile Ala Leu Asn
305                 310                 315                 320

Thr Ala Leu Ala Gln Leu Gly Val Val Arg Pro Val Phe Arg Leu Pro
                325                 330                 335

Tyr Val Pro Leu Pro Leu Glu Lys Arg Val Glu Phe Val Arg Ile Val
                340                 345                 350

Glu Ser Ile Gly Arg Glu Asn Phe Val Gly Glu Asn Glu Ala Arg Val
            355                 360                 365

Leu Asp Asp Asp Phe Val Leu Val Ser Arg Tyr
    370                 375                 380
```

```
<210> SEQ ID NO 3
<211> LENGTH: 25
<212> TYPE: DNA
<213> ORGANISM: Oryza sativa

<400> SEQUENCE: 3
gtaatagttg gaggaacaac aggag                                        25

<210> SEQ ID NO 4
<211> LENGTH: 24
<212> TYPE: DNA
<213> ORGANISM: Oryza sativa

<400> SEQUENCE: 4
gagctgagcc agagcagtgt tgag                                         24

<210> SEQ ID NO 5
<211> LENGTH: 1143
<212> TYPE: DNA
<213> ORGANISM: Oryza sativa
<220> FEATURE:
<221> NAME/KEY: CDS
<222> LOCATION: (1)..(1143)

<400> SEQUENCE: 5 atg gcg tcg ctg ctg atc gcc agc acg ggg ggc tgc cca ccg cct cgc    48
Met Ala Ser Leu Leu Ile Ala Ser Thr Gly Gly Cys Pro Pro Pro Arg
1               5                   10                  15 gtg gaa gga cgc cgc cgc cct ggg acc cgc tcc ggc ttg gcg cga cct    96
Val Glu Gly Arg Arg Arg Pro Gly Thr Arg Ser Gly Leu Ala Arg Pro
                20                  25                  30 tgg ccc gcc gcc gtg gct gca ccg gcg ccg ctg ctc agg att agc aga   144
Trp Pro Ala Ala Val Ala Ala Pro Ala Pro Leu Leu Arg Ile Ser Arg
            35                  40                  45 gga aag ttt gca ttg cag gcc atc acc ctt gat gat tat ctt cca atg   192
Gly Lys Phe Ala Leu Gln Ala Ile Thr Leu Asp Asp Tyr Leu Pro Met
        50                  55                  60
```

```
cga agt act gaa gtg aaa aat cgg aca tca aca gct gat atc act agt      240
Arg Ser Thr Glu Val Lys Asn Arg Thr Ser Thr Ala Asp Ile Thr Ser
 65              70                  75                  80 ctc aga gta att aca gcg gtc aaa acc cca tat ctg cct gat gga aga      288
Leu Arg Val Ile Thr Ala Val Lys Thr Pro Tyr Leu Pro Asp Gly Arg
                 85                  90                  95 ttt gat ctc gaa gca tat gat tca ctg ata aat atg cag ata gat ggt      336
Phe Asp Leu Glu Ala Tyr Asp Ser Leu Ile Asn Met Gln Ile Asp Gly
            100                 105                 110 ggt gct gaa ggt gta ata gtt gga gga aca aca gga gag ggc cac ctt      384
Gly Ala Glu Gly Val Ile Val Gly Gly Thr Thr Gly Glu Gly His Leu
        115                 120                 125 atg agc tgg gat gaa cac atc atg ctt att gga cat act gtt aac tgc      432
Met Ser Trp Asp Glu His Ile Met Leu Ile Gly His Thr Val Asn Cys
    130                 135                 140 ttt ggt gct aaa gtt aaa gtg gta ggc aac aca ggt agt atc tca aca      480
Phe Gly Ala Lys Val Lys Val Val Gly Asn Thr Gly Ser Ile Ser Thr
145                 150                 155                 160 aga gag gct att cat gca aca gag cag gga ttt gct gta ggt atg cat      528
Arg Glu Ala Ile His Ala Thr Glu Gln Gly Phe Ala Val Gly Met His
                165                 170                 175 gcg gct ctc cat atc aat cct tac tat ggg aag acc tct atc gaa ggg      576
Ala Ala Leu His Ile Asn Pro Tyr Tyr Gly Lys Thr Ser Ile Glu Gly
            180                 185                 190 ttg ata tct cat ttt gag gct gtc ctc cca atg ggt cca acc att att      624
Leu Ile Ser His Phe Glu Ala Val Leu Pro Met Gly Pro Thr Ile Ile
        195                 200                 205 tac aat gtt cca tct agg act ggc cag gat att cct cct gca gtt att      672
Tyr Asn Val Pro Ser Arg Thr Gly Gln Asp Ile Pro Pro Ala Val Ile
    210                 215                 220 gag gct gtt tca agt ttc aca aac ttg gca ggt gtg aaa gaa tgt gtt      720
Glu Ala Val Ser Ser Phe Thr Asn Leu Ala Gly Val Lys Glu Cys Val
225                 230                 235                 240 gga cat gag agg gtt aag tgc tac act gac aaa ggt ata acc ata tgg      768
Gly His Glu Arg Val Lys Cys Tyr Thr Asp Lys Gly Ile Thr Ile Trp
                245                 250                 255 agt ggt aat gat gat gaa tgc cat gat tct agg tgg aaa tat ggt gcc      816
Ser Gly Asn Asp Asp Glu Cys His Asp Ser Arg Trp Lys Tyr Gly Ala
            260                 265                 270 act gga gtt att tct gtg gct agc aac ctt att cct ggt ctc atg cac      864
Thr Gly Val Ile Ser Val Ala Ser Asn Leu Ile Pro Gly Leu Met His
        275                 280                 285 gat ctc atg tat gaa ggg gag aat aag acg cta aat gag aag ctc ttt      912
Asp Leu Met Tyr Glu Gly Glu Asn Lys Thr Leu Asn Glu Lys Leu Phe
    290                 295                 300 ccc ctg atg aaa tgg ttg ttt tgc cag cca aat cca att gct ctc aac      960
Pro Leu Met Lys Trp Leu Phe Cys Gln Pro Asn Pro Ile Ala Leu Asn
305                 310                 315                 320 act gcc ctg gct cag ctt gga gtg gta agg cct gtt ttc aga tta cca     1008
Thr Ala Leu Ala Gln Leu Gly Val Val Arg Pro Val Phe Arg Leu Pro
                325                 330                 335 tat gta cct ctt cct ctt gaa aag agg gta gag ttt gtc cga atc gtt     1056
Tyr Val Pro Leu Pro Leu Glu Lys Arg Val Glu Phe Val Arg Ile Val
            340                 345                 350 gaa tct att gga cgg gaa aac ttt gtg ggt gag aac gag gca cgg gtt     1104
Glu Ser Ile Gly Arg Glu Asn Phe Val Gly Glu Asn Glu Ala Arg Val
        355                 360                 365 ctt gac gac gat gat ttt gtg ttg gtc agt agg tac taa                 1143
Leu Asp Asp Asp Asp Phe Val Leu Val Ser Arg Tyr
```

-continued

```
         370                 375                 380
```

<210> SEQ ID NO 6
<211> LENGTH: 380
<212> TYPE: PRT
<213> ORGANISM: Oryza sativa

<400> SEQUENCE: 6

```
Met Ala Ser Leu Leu Ile Ala Ser Thr Gly Gly Cys Pro Pro Arg
1               5                   10                  15

Val Glu Gly Arg Arg Pro Gly Thr Arg Ser Gly Leu Ala Arg Pro
            20                  25                  30

Trp Pro Ala Ala Val Ala Ala Pro Ala Pro Leu Leu Arg Ile Ser Arg
        35                  40                  45

Gly Lys Phe Ala Leu Gln Ala Ile Thr Leu Asp Asp Tyr Leu Pro Met
    50                  55                  60

Arg Ser Thr Glu Val Lys Asn Arg Thr Ser Thr Ala Asp Ile Thr Ser
65                  70                  75                  80

Leu Arg Val Ile Thr Ala Val Lys Thr Pro Tyr Leu Pro Asp Gly Arg
                85                  90                  95

Phe Asp Leu Glu Ala Tyr Asp Ser Leu Ile Asn Met Gln Ile Asp Gly
            100                 105                 110

Gly Ala Glu Gly Val Ile Val Gly Gly Thr Thr Gly Glu Gly His Leu
        115                 120                 125

Met Ser Trp Asp Glu His Ile Met Leu Ile Gly His Thr Val Asn Cys
130                 135                 140

Phe Gly Ala Lys Val Lys Val Val Gly Asn Thr Gly Ser Ile Ser Thr
145                 150                 155                 160

Arg Glu Ala Ile His Ala Thr Glu Gln Gly Phe Ala Val Gly Met His
                165                 170                 175

Ala Ala Leu His Ile Asn Pro Tyr Tyr Gly Lys Thr Ser Ile Glu Gly
            180                 185                 190

Leu Ile Ser His Phe Glu Ala Val Leu Pro Met Gly Pro Thr Ile Ile
        195                 200                 205

Tyr Asn Val Pro Ser Arg Thr Gly Gln Asp Ile Pro Pro Ala Val Ile
    210                 215                 220

Glu Ala Val Ser Ser Phe Thr Asn Leu Ala Gly Val Lys Glu Cys Val
225                 230                 235                 240

Gly His Glu Arg Val Lys Cys Tyr Thr Asp Lys Gly Ile Thr Ile Trp
                245                 250                 255

Ser Gly Asn Asp Asp Glu Cys His Asp Ser Arg Trp Lys Tyr Gly Ala
            260                 265                 270

Thr Gly Val Ile Ser Val Ala Ser Asn Leu Ile Pro Gly Leu Met His
        275                 280                 285

Asp Leu Met Tyr Glu Gly Glu Asn Lys Thr Leu Asn Glu Lys Leu Phe
    290                 295                 300

Pro Leu Met Lys Trp Leu Phe Cys Gln Pro Asn Pro Ile Ala Leu Asn
305                 310                 315                 320

Thr Ala Leu Ala Gln Leu Gly Val Val Arg Pro Val Phe Arg Leu Pro
                325                 330                 335

Tyr Val Pro Leu Pro Leu Glu Lys Arg Val Glu Phe Val Arg Ile Val
            340                 345                 350

Glu Ser Ile Gly Arg Glu Asn Phe Val Gly Glu Asn Glu Ala Arg Val
        355                 360                 365
```

```
Leu Asp Asp Asp Phe Val Leu Val Ser Arg Tyr
    370             375             380
```

<210> SEQ ID NO 7
<211> LENGTH: 1143
<212> TYPE: DNA
<213> ORGANISM: Oryza sativa
<220> FEATURE:
<221> NAME/KEY: CDS
<222> LOCATION: (1)..(1143)

<400> SEQUENCE: 7

```
atg gcg tcg ctg ctg atc gcc agc acg ggg ggc tgc cca ccg cct cgc      48
Met Ala Ser Leu Leu Ile Ala Ser Thr Gly Gly Cys Pro Pro Pro Arg
1               5                   10                  15 gtg gaa gga cgc cgc cgc cct ggg acc cgc tcc ggc ttg gcg cga cct      96
Val Glu Gly Arg Arg Arg Pro Gly Thr Arg Ser Gly Leu Ala Arg Pro
            20                  25                  30 tgg ccc gcc gcc gtg gct gca ccg gcg ccg ctg ctc agg att agc aga     144
Trp Pro Ala Ala Val Ala Ala Pro Ala Pro Leu Leu Arg Ile Ser Arg
        35                  40                  45 gga aag ttt gca ttg cag gcc atc acc ctt gat gat tat ctt cca atg     192
Gly Lys Phe Ala Leu Gln Ala Ile Thr Leu Asp Asp Tyr Leu Pro Met
    50                  55                  60 cga agt act gaa gtg aaa aat cgg aca tca aca gct gat atc act agt     240
Arg Ser Thr Glu Val Lys Asn Arg Thr Ser Thr Ala Asp Ile Thr Ser
65                  70                  75                  80 ctc aga gta att aca gcg gtc aaa acc cca tat ctg cct gat gga aga     288
Leu Arg Val Ile Thr Ala Val Lys Thr Pro Tyr Leu Pro Asp Gly Arg
                85                  90                  95 ttt gat ctc gaa gca tat gat tca ctg ata aat atg cag ata gat ggt     336
Phe Asp Leu Glu Ala Tyr Asp Ser Leu Ile Asn Met Gln Ile Asp Gly
            100                 105                 110 ggt gct gaa ggt gta ata gtt gga gga aca aca gga gag ggc cac ctt     384
Gly Ala Glu Gly Val Ile Val Gly Gly Thr Thr Gly Glu Gly His Leu
        115                 120                 125 atg agc tgg gat gaa cac atc atg ctt att gga cat act gtt aac tgc     432
Met Ser Trp Asp Glu His Ile Met Leu Ile Gly His Thr Val Asn Cys
    130                 135                 140 ttt ggt gct aaa gtt aaa gtg gta ggc aac aca ggt agt aac tca aca     480
Phe Gly Ala Lys Val Lys Val Val Gly Asn Thr Gly Ser Asn Ser Thr
145                 150                 155                 160 aga gag gct att cat gta aca gag cag gga ttt gct gta ggt atg cat     528
Arg Glu Ala Ile His Val Thr Glu Gln Gly Phe Ala Val Gly Met His
                165                 170                 175 gcg gct ctc cat atc aat cct tac tat ggg aag acc tct atc gaa ggg     576
Ala Ala Leu His Ile Asn Pro Tyr Tyr Gly Lys Thr Ser Ile Glu Gly
            180                 185                 190 ttg ata tct cat ttt gag gct gtc ctc cca atg ggt cca acc att att     624
Leu Ile Ser His Phe Glu Ala Val Leu Pro Met Gly Pro Thr Ile Ile
        195                 200                 205 tac aat gtt cca tct agg act ggc cag gat att cct cct gca gtt att     672
Tyr Asn Val Pro Ser Arg Thr Gly Gln Asp Ile Pro Pro Ala Val Ile
    210                 215                 220 gag gct gtt tca agt ttc aca aac ttg gca ggt gtg aaa gaa tgt gtt     720
Glu Ala Val Ser Ser Phe Thr Asn Leu Ala Gly Val Lys Glu Cys Val
225                 230                 235                 240 gga cat gag agg gtt aag tgc tac act gac aaa ggt ata acc ata tgg     768
Gly His Glu Arg Val Lys Cys Tyr Thr Asp Lys Gly Ile Thr Ile Trp
                245                 250                 255 agt ggt aat gat gat gaa tgc cat gat tct agg tgg aaa tat ggt gcc     816
```

-continued

```
Ser Gly Asn Asp Asp Glu Cys His Asp Ser Arg Trp Lys Tyr Gly Ala
            260                 265                 270 act gga gtt att tct gtg gct agc aac ctt att cct ggt ctc atg cac      864
Thr Gly Val Ile Ser Val Ala Ser Asn Leu Ile Pro Gly Leu Met His
            275                 280                 285 gat ctc atg tat gaa ggg gag aat aag acg cta aat gag aag ctc ttt      912
Asp Leu Met Tyr Glu Gly Glu Asn Lys Thr Leu Asn Glu Lys Leu Phe
290                 295                 300 ccc ctg atg aaa tgg ttg ttt tgc cag cca aat cca att gct ctc aac      960
Pro Leu Met Lys Trp Leu Phe Cys Gln Pro Asn Pro Ile Ala Leu Asn
305                 310                 315                 320 act gcc ctg gct cag ctt gga gtg gta agg cct gtt ttc aga tta cca     1008
Thr Ala Leu Ala Gln Leu Gly Val Val Arg Pro Val Phe Arg Leu Pro
                325                 330                 335 tat gta cct ctt cct ctt gaa aag agg gta gag ttt gtc cga atc gtt     1056
Tyr Val Pro Leu Pro Leu Glu Lys Arg Val Glu Phe Val Arg Ile Val
            340                 345                 350 gaa tct att gga cgg gaa aac ttt gtg ggt gag aac gag gca cgg gtt     1104
Glu Ser Ile Gly Arg Glu Asn Phe Val Gly Glu Asn Glu Ala Arg Val
        355                 360                 365 ctt gac gac gat gat ttt gtg ttg gtc agt agg tac taa                 1143
Leu Asp Asp Asp Asp Phe Val Leu Val Ser Arg Tyr
    370                 375                 380
```

<210> SEQ ID NO 8
<211> LENGTH: 380
<212> TYPE: PRT
<213> ORGANISM: Oryza sativa

<400> SEQUENCE: 8

```
Met Ala Ser Leu Leu Ile Ala Ser Thr Gly Gly Cys Pro Pro Arg
1               5                   10                  15

Val Glu Gly Arg Arg Pro Gly Thr Arg Ser Gly Leu Ala Arg Pro
                20                  25                  30

Trp Pro Ala Ala Val Ala Ala Pro Ala Pro Leu Leu Arg Ile Ser Arg
            35                  40                  45

Gly Lys Phe Ala Leu Gln Ala Ile Thr Leu Asp Asp Tyr Leu Pro Met
    50                  55                  60

Arg Ser Thr Glu Val Lys Asn Arg Thr Ser Thr Ala Asp Ile Thr Ser
65                  70                  75                  80

Leu Arg Val Ile Thr Ala Val Lys Thr Pro Tyr Leu Pro Asp Gly Arg
                85                  90                  95

Phe Asp Leu Glu Ala Tyr Asp Ser Leu Ile Asn Met Gln Ile Asp Gly
            100                 105                 110

Gly Ala Glu Gly Val Ile Val Gly Gly Thr Thr Gly Glu Gly His Leu
        115                 120                 125

Met Ser Trp Asp Glu His Ile Met Leu Ile Gly His Thr Val Asn Cys
    130                 135                 140

Phe Gly Ala Lys Val Lys Val Val Gly Asn Thr Gly Ser Asn Ser Thr
145                 150                 155                 160

Arg Glu Ala Ile His Val Thr Glu Gln Gly Phe Ala Val Gly Met His
                165                 170                 175

Ala Ala Leu His Ile Asn Pro Tyr Tyr Gly Lys Thr Ser Ile Glu Gly
            180                 185                 190

Leu Ile Ser His Phe Glu Ala Val Leu Pro Met Gly Pro Thr Ile Ile
        195                 200                 205

Tyr Asn Val Pro Ser Arg Thr Gly Gln Asp Ile Pro Pro Ala Val Ile
```

-continued

```
              210                 215                 220
Glu Ala Val Ser Ser Phe Thr Asn Leu Ala Gly Val Lys Glu Cys Val
225                 230                 235                 240

Gly His Glu Arg Val Lys Cys Tyr Thr Asp Lys Gly Ile Thr Ile Trp
                245                 250                 255

Ser Gly Asn Asp Asp Glu Cys His Asp Ser Arg Trp Lys Tyr Gly Ala
                260                 265                 270

Thr Gly Val Ile Ser Val Ala Ser Asn Leu Ile Pro Gly Leu Met His
                275                 280                 285

Asp Leu Met Tyr Glu Gly Glu Asn Lys Thr Leu Asn Glu Lys Leu Phe
290                 295                 300

Pro Leu Met Lys Trp Leu Phe Cys Gln Pro Asn Pro Ile Ala Leu Asn
305                 310                 315                 320

Thr Ala Leu Ala Gln Leu Gly Val Val Arg Pro Val Phe Arg Leu Pro
                325                 330                 335

Tyr Val Pro Leu Pro Leu Glu Lys Arg Val Glu Phe Val Arg Ile Val
                340                 345                 350

Glu Ser Ile Gly Arg Glu Asn Phe Val Gly Glu Asn Glu Ala Arg Val
                355                 360                 365

Leu Asp Asp Asp Asp Phe Val Leu Val Ser Arg Tyr
370                 375                 380
```

<210> SEQ ID NO 9
<211> LENGTH: 32
<212> TYPE: DNA
<213> ORGANISM: Oryza sativa

<400> SEQUENCE: 9
gcctctcttg ttgagatact acctgtgttg cc                                32

<210> SEQ ID NO 10
<211> LENGTH: 30
<212> TYPE: DNA
<213> ORGANISM: Oryza sativa

<400> SEQUENCE: 10
gcaaatccct gctctgttac atgaatagcc                                   30

<210> SEQ ID NO 11
<211> LENGTH: 20
<212> TYPE: DNA
<213> ORGANISM: Oryza sativa

<400> SEQUENCE: 11
gtaaaacgac ggccagtgag                                              20

<210> SEQ ID NO 12
<211> LENGTH: 19
<212> TYPE: DNA
<213> ORGANISM: Oryza sativa

<400> SEQUENCE: 12
ggaaacagct atgaccatg                                               19

<210> SEQ ID NO 13
<211> LENGTH: 21
<212> TYPE: DNA
<213> ORGANISM: Oryza sativa

<400> SEQUENCE: 13

```
tagggcgaat tgtgtgtacc g                                              21

<210> SEQ ID NO 14
<211> LENGTH: 30
<212> TYPE: DNA
<213> ORGANISM: Oryza sativa

<400> SEQUENCE: 14
gctctagaca agatggcgtc gctgctgatc                                     30

<210> SEQ ID NO 15
<211> LENGTH: 28
<212> TYPE: DNA
<213> ORGANISM: Oryza sativa

<400> SEQUENCE: 15
gcgagctcgt tagtacctac tgaccaac                                       28
```